United States Patent [19]
Burton et al.

[11] Patent Number: 6,156,313
[45] Date of Patent: Dec. 5, 2000

[54] HUMAN MONOCLONAL ANTIBODIES TO HERPES SIMPLEX VIRUS AND METHODS THEREFOR

[75] Inventors: Dennis R. Burton, La Jolla; Robert A. Williamson, Del Mar, both of Calif.; Roberto Burioni, Fermignano, Italy; Pietro Paolo Sanna, San Diego, Calif.

[73] Assignee: The Scripps Research Institute, La Jolla, Calif.

[21] Appl. No.: 08/852,147

[22] Filed: May 6, 1997

Related U.S. Application Data

[63] Continuation of application No. 08/178,201, Jan. 4, 1994, abandoned.

[51] Int. Cl.[7] .................. C07K 16/08; A61K 39/395; G01N 33/53
[52] U.S. Cl. ................ 424/147.1; 435/7.1; 530/388.15; 530/388.3; 530/387.3; 424/142.1
[58] Field of Search ............................ 424/142.1, 147.1; 435/7.1; 530/388.15, 388.3, 387.3

[56] References Cited

PUBLICATIONS

Waldmann Science vol. 252 p. 1657, 1991.
Harris et al. TibTech vol. 11 p. 42 1993.
Hird et al. Genes and Cancer Ed. Carney et al. 1990 p. 183.
Williamson et al. PNAS vol. 90, p. 4141 1993.
Journal of General Virology 67, p. 1001 1986.
Cohen et al. Journal of Virology p. 102, 1984.
Barbas et al PNAS 88:7978 1991.
Hoogenboom et al. Nucleic Acids Research vol. 19 No. 15 4133 1991.
Seigneurin et al. Science vol. 221, 173 issued Jul. 8, 1983.

*Primary Examiner*—Toni R. Scheiner
*Assistant Examiner*—Nancy A. Johnson
*Attorney, Agent, or Firm*—Thomas Fitting

[57] ABSTRACT

The present invention describes human monoclonal antibodies which immunoreact with Herpes simplex virus Type-1 and Type-2. Also disclosed are immunotherapeutic and diagnostic methods of using the monoclonal antibodies, as well as nucleic acids and cell lines for producing the monoclonal antibodies.

8 Claims, 8 Drawing Sheets

SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
      (A) LENGTH: 16 amino acids
      (B) TYPE: amino acid
      (C) STRANDEDNESS: single
      (D) TOPOLOGY: linear (ii) MOLECULE TYPE: peptide (vii) IMMEDIATE SOURCE:
      (B) CLONE: FabHSV 8-CDR3

(ix) FEATURE:
      (A) NAME/KEY: Peptide
      (B) LOCATION: 1..16

(xi) SEQUENCE DESCRIPTION: SEQ ID NO:1:

Val Ala Tyr Met Leu Glu Pro Thr Val Thr Ala Gly Gly Leu Asp Val
  1              5                  10               15

(2) INFORMATION FOR SEQ ID NO:2:

(i) SEQUENCE CHARACTERISTICS:
      (A) LENGTH: 122 amino acids
      (B) TYPE: amino acid
      (C) STRANDEDNESS: single
      (D) TOPOLOGY: linear (ii) MOLECULE TYPE: peptide (vii) IMMEDIATE SOURCE:
      (B) CLONE: FabHSV 8

(ix) FEATURE:
      (A) NAME/KEY: Peptide
      (B) LOCATION: 1..122

(xi) SEQUENCE DESCRIPTION: SEQ ID NO:2:

Leu Glu Gln Ser Gly Ala Glu Val Lys Lys Pro Gly Ser Ser Val Lys
  1              5                  10               15

Val Ser Cys Lys Ala Ser Gly Gly Ser Phe Ser Ser Tyr Ala Ile Asn
             20                  25                 30

Trp Val Arg Gln Ala Pro Gly Gln Gly Leu Glu Trp Met Gly Gly Leu
             35                  40                 45

Met Pro Ile Phe Gly Thr Thr Asn Tyr Ala Gln Lys Phe Gln Asp Arg
      50                  55                 60

Leu Thr Ile Thr Ala Asp Val Ser Thr Ser Thr Ala Tyr Met Gln Leu
   65                 70                 75              80

Ser Gly Leu Thr Tyr Glu Asp Thr Ala Met Tyr Tyr Cys Ala Arg Val
                     85                  90               95

Ala Tyr Met Leu Glu Pro Thr Val Thr Ala Gly Gly Leu Asp Val Trp
                 100                105              110

Gly Gln Gly Thr Thr Val Thr Val Ala Ser
            115                  120

(2) INFORMATION FOR SEQ ID NO:3:

(i) SEQUENCE CHARACTERISTICS:
      (A) LENGTH: 32 base pairs (B) TYPE: nucleic acid
            (C) STRANDEDNESS: single
            (D) TOPOLOGY: linear (ii) MOLECULE TYPE: DNA (genomic)

(vii) IMMEDIATE SOURCE:
            (B) CLONE: N1

(ix) FEATURE:
            (A) NAME/KEY: CDS
            (B) LOCATION: 1..32

(xi) SEQUENCE DESCRIPTION: SEQ ID NO:3:

GGCCGCAAAT TCTATTTCAA GGAGACAGTC AT                                          32

(2) INFORMATION FOR SEQ ID NO:4:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (genomic)

(vii) IMMEDIATE SOURCE:
            (B) CLONE: N2

(ix) FEATURE:
            (A) NAME/KEY: CDS
            (B) LOCATION: 1..36

(xi) SEQUENCE DESCRIPTION: SEQ ID NO:4:

AATGAAATAC CTATTGCCTA CGGCAGCCGC TGGATT                                      36

(2) INFORMATION FOR SEQ ID NO:5:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (genomic)

(vii) IMMEDIATE SOURCE:
            (B) CLONE: N3

(ix) FEATURE:
            (A) NAME/KEY: CDS
            (B) LOCATION: 1..32

(xi) SEQUENCE DESCRIPTION: SEQ ID NO:5:

GTTATTACTC GCTGCCCAAC CAGCCATGGC CC                                          32

(2) INFORMATION FOR SEQ ID NO:6:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (genomic)

(vii) IMMEDIATE SOURCE:
            (B) CLONE: N6

(ix) FEATURE:
            (A) NAME/KEY: CDS
            (B) LOCATION: 1..29

(xi) SEQUENCE DESCRIPTION: SEQ ID NO:6:

CAGTTTCACC TGGGCCATGG CTGGTTGGG                                              29

(2) INFORMATION FOR SEQ ID NO:7:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: N7

(ix) FEATURE:
        (A) NAME/KEY: CDS
        (B) LOCATION: 1..40

(xi) SEQUENCE DESCRIPTION: SEQ ID NO:7:

CAGCGAGTAA TAACAATCCA GCGGCTGCCG TAGGCAATAG                                   40

(2) INFORMATION FOR SEQ ID NO:8:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: N8

(ix) FEATURE:
        (A) NAME/KEY: CDS
        (B) LOCATION: 1..38

(xi) SEQUENCE DESCRIPTION: SEQ ID NO:8:

GTATTTCATT ATGACTGTCT CCTTGAAATA GAATTTGC                                     38

(2) INFORMATION FOR SEQ ID NO:9:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: N9-4

(ix) FEATURE:
        (A) NAME/KEY: CDS
        (B) LOCATION: 1..40

(xi) SEQUENCE DESCRIPTION: SEQ ID NO:9:

AGGTGAAACT GCTCGAGATT TCTAGACTAG TTACCCGTAC                                   40

(2) INFORMATION FOR SEQ ID NO:10:

(i) SEQUENCE CHARACTERISTICS:
        (A) LENGTH: 38 base pairs
        (B) TYPE: nucleic acid
        (C) STRANDEDNESS: single
        (D) TOPOLOGY: linear

```
    (ii) MOLECULE TYPE: DNA (genomic)

(vii) IMMEDIATE SOURCE:
        (B) CLONE: N10-5

(ix) FEATURE:
        (A) NAME/KEY: CDS
        (B) LOCATION: 1..38

(xi) SEQUENCE DESCRIPTION: SEQ ID NO:10:

CGGAACGTCG TACGGGTAAC TAGTCTAGAA ATCTCGAG                                38

(2) INFORMATION FOR SEQ ID NO:11:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: N11

(ix) FEATURE:
        (A) NAME/KEY: CDS
        (B) LOCATION: 1..33

(xi) SEQUENCE DESCRIPTION: SEQ ID NO:11:

GACGTTCCGG ACTACGGTTC TTAATAGAAT TCG                                     33

(2) INFORMATION FOR SEQ ID NO:12:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: N12

(ix) FEATURE:
        (A) NAME/KEY: CDS
        (B) LOCATION: 1..28

(xi) SEQUENCE DESCRIPTION: SEQ ID NO:12:

TCGACGAATT CTATTAAGAA CCGTAGTC                                           28

(2) INFORMATION FOR SEQ ID NO:13:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..34

(xi) SEQUENCE DESCRIPTION: SEQ ID NO:13:

TGAATTCTAA ACTAGTCGCC AAGGAGACAG TCAT                                    34

(2) INFORMATION FOR SEQ ID NO:14:
```

```
    (i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..36

(xi) SEQUENCE DESCRIPTION: SEQ ID NO:14:

AATGAAATAC CTATTGCCTA CGGCAGCCGC TGGATT                                36

(2) INFORMATION FOR SEQ ID NO:15:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..31

(xi) SEQUENCE DESCRIPTION: SEQ ID NO:15:

GTTATTACTC GCTGCCCAAC CAGCCATGGC C                                     31

(2) INFORMATION FOR SEQ ID NO:16:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..30

(xi) SEQUENCE DESCRIPTION: SEQ ID NO:16:

GAGCTCGTCA GTTCTAGAGT TAAGCGGCCG                                       30

(2) INFORMATION FOR SEQ ID NO:17:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..48

(xi) SEQUENCE DESCRIPTION: SEQ ID NO:17:

CTATTTCATT ATGACTGTCT CCTTGGCGAC TAGTTTAGAA TTCAAGCT                   48

(2) INFORMATION FOR SEQ ID NO:18:

(i) SEQUENCE CHARACTERISTICS:
        (A) LENGTH: 40 base pairs
        (B) TYPE: nucleic acid
```

(C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..40

(xi) SEQUENCE DESCRIPTION: SEQ ID NO:18:

CAGCGAGTAA TAACAATCCA GCGGCTGCCG TAGGCAATAG                              40

(2) INFORMATION FOR SEQ ID NO:19:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..27

(xi) SEQUENCE DESCRIPTION: SEQ ID NO:19:

TGACGAGCTC GGCCATGGCT GGTTGGG                                           27

(2) INFORMATION FOR SEQ ID NO:20:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..24

(xi) SEQUENCE DESCRIPTION: SEQ ID NO:20:

TCGACGGCCG CTTAACTCTA GAAC                                              24

(2) INFORMATION FOR SEQ ID NO:21:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..48

(xi) SEQUENCE DESCRIPTION: SEQ ID NO:21:

GAGACGACTA GTGGTGGCGG TGGCTCTCCA TTCGTTTGTG AATATCAA                    48

(2) INFORMATION FOR SEQ ID NO:22:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..40

(xi) SEQUENCE DESCRIPTION: SEQ ID NO:22:

TTACTAGCTA GCATAATAAC GGAATACCCA AAAGAACTGG					40

(2) INFORMATION FOR SEQ ID NO:23:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..36

(xi) SEQUENCE DESCRIPTION: SEQ ID NO:23:

TATGCTAGCT AGTAACACGA CAGGTTTCCC GACTGG					36

(2) INFORMATION FOR SEQ ID NO:24:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..27

(xi) SEQUENCE DESCRIPTION: SEQ ID NO:24:

ACCGAGCTCG AATTCGTAAT CATGGTC					27

(2) INFORMATION FOR SEQ ID NO:25:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..31

(xi) SEQUENCE DESCRIPTION: SEQ ID NO:25:

AGCTGTTGAA TTCGTGAAAT TGTTATCCGC T					31

HUMAN MONOCLONAL ANTIBODIES TO HERPES SIMPLEX VIRUS AND METHODS THEREFOR

This is a continuation of application Ser. No. 08/178,201, filed Jan. 4, 1994, now abandoned.

This invention was made with Government support under grant No. 1RO1 A133292-01 ARRA and NIMH 47680 from the National Institutes of Health. The Government has certain rights in this invention.

BACKGROUND OF THE INVENTION

1. Field of the Invention

This invention relates generally to field of immunology and specifically to human monoclonal antibodies which bind and neutralize Herpes simplex virus (HSV) Type-1 and Type-2.

2. Description of Related Art

Herpes simplex virus (HSV) remains one of the most common viral maladies in man, achieving a worldwide distribution and causing a variety of infections. Two forms of the virus, HSV Type-1 (HSV-1) and HSV Type-2 (HSV-2), have been distinguished by clinical, biochemical, and serological criteria. HSV-2 is more commonly implicated in genital infection, while HSV-1 is associated with oral and ocular disease. Both types of the virus may become latent after traveling intranasally to sensory ganglia.

Primary and secondary herpes infections in individuals immunocompromised by underlying disease or immunosupressive drugs are often more severe than in the normal host. Such individuals, which include AIDS patients, those with hematological or lymphoreticular neoplasms, (Siegal, et al., *N. Engl. J. Med.*, 305:1439–1444, 1981; Greenberg, et al.,*J. Infect. Dis.*, 156:280–287, 1987; Buss, et al., *J.A.M.A.*, 243:1903–1905, 1980) and organ and bone marrow transplant recipients, are also prone to increased frequency of secondary herpes episodes. In the case of transplant recipients, the severity of herpes infection correlates with the degree of immunosuppressive therapy employed (Rand, et al., *N. Engl. J. Med.*, 296:1372–1377, 1977).

Devastating illness may also result from HSV infection of the neonate. In the U.S., such infections are encountered in 1 in 2,500 to 1 in 5,000 deliveries per year, most being acquired following intrapartum contact with infected genital secretions (Whitley, *Virology eds.*, 2nd Eds:1843–1889, 1990). As compared to a recurrent episode, primary infection occurring late in pregnancy generally produces more frequent and severe disease in the newborn. This correlates with a greater maternal viral load at delivery (Corey, et al., *Ann. Intem. Med.*, 98:958–972, 1983), probably arising because the immune reponse to the virus is only in its early stages.

Current therapy of herpes infections is limited, although acyclovir, vidarabine and related drugs have proven useful for the management of specific infections such as mucocutaneous herpes infections in the immunocompromised host, herpes simplex encephalitis and neonatal herpes. Recurrent episodes, however, are less responsive. Moreover, viral strains resistant to these drugs have been isolated from immunocompromised patients (Englund, et al., *Ann. Int. Med.*, 112:416–422, 1990; Sacks, et al., supra; Erlich, et al., *N. Engl. J. Med.*, 320:293–296, 1989). A potential alternative approcah to HSV prevention and therapy is offered by specific human antibodies to the virus. Such reagents, if highly efficient in virus neutralization and in mediating the clearance of virally infected cells, may prove useful in replacing or complementing existing clinical regimes.

There is evidence of a significant protective role for antibody in human infection in vivo. The presence of neutralizing antibody in acute phase serum during primary infections has been associated with reduced severity and duration of the primarly genital herpes episode (Core, *J.A.M.A.*, 248:1041–1049, 1982). Further, it has been shown that the development of recurrent genital herpes in an individual following a primary infection with homologous virus is inversely correlated with the titer of HSV-2 neutralizing antibody in the convalescent serum (Reeves, et al., *N. Engl. J. Med.*, 305:315–319, 1981). Moreover, the titer of anti-HSV antibodies in bone marrow transplant recipients is predictive of the risk of infection (Pass, et al.,*J. Infect. Dis.*, 140:487–491, 1979). In vitro, human serum antibody has additionally been shown to neutralize extra-cellular virus and lyse certain HSV-infected cells (Allison, *Transplant Ref.*, 19:3–55, 1974).

HSV is a complex virus. Over 50 virus encoded polypeptides, including both structural (envelope and core) and regulatory proteins, have been identified in infected cells. Analysis of the humoral response against HSV and the identification and characterization of potentially protective antigens has been undertaken largely using human sera and mouse monoclonal antibodies (Fujinaga, et al., *J. Infect. Dis.*, 155:45–53, 1987; Kapoor, et al., *J. Gen. Virol.*, 60:225–233, 1982; Kumel, et al., *J. Virol.*, 56:930–937, 1985; Rector, et al., *J. Fen. Virol.*, 65:657–661, 1984; Simmons, et al.,*J. Virol.*, 53:944–948, 1985; Kuhn, et al.,*J. Med. Virol.*, 23:135–150, 1987). The main targets of the humoral and cellular responses appear to be the 7 well characterized HSV envelope glycoproteins, gB, gC, gD, gE, gG, gH and gI, which are found both on the virion and on the infected cell surface where they are thought to promote viral attachment and penetration through multiple interactions between themselves and the cell membrane. Only gB, gD and gH have been found to be indispensable for viral growth in cell culture. Virus mutants defective in these molecules will bind to the host cell surface, but are unable to penetrate into the cytoplasm (Desai, et al., *J. Gen. Virol.*, 69:1147–1156, 1988; Fuller, et al.,*J. Virol.*, 63:3435–3443, 1989; Ugas, et al.,*J. Virol.*, 62:1486–1494, 1988; Weber, et al., *Science*, 236:576579, 1987). Those glycoproteins which are mandatory for virus attachment have not yet been identified.

Each envelope glycoprotein is capable of eliciting mouse monoclonal antibodies able to neutralize virus in vitro (Whitley, et al., *Virology eds.*, 2nd Ed:1843–1889, 1990). Passive immunization with monoclonal antibodies specific for gB, gC, gD, gE and gH has also been shown to protect animals from infection (Kumel, et al.,*J. Virol.*, 56:930–937, 1985; Simmons, et al., *J. Virol.*, 53:944–948, 1985; Balachandran, et al., *Infect. Immun.*, 37:1132–1137, 1982; Dix, et al., *Infect Immun.*, 34:192–199, 1981). In addition, polyclonal immune sera and gD specific monoclonal antibodies have been shown to protect mice from recurrent disease (Simmons, et al.,*J. Virol.*, 53:944–948, 1985). It has also been demonstrated that monoclonal antibodies against gB and gE suppress the replication of HSV-1 in trigeminal ganglia (Oakes, et al., *J. Virol.*, 51:656–661, 1984). Glycoproteins B and D appear to elicit a major part of the antibody response to virus in humans and also appear to be the major targets of neutralizing antibodies (Kuhn, et al., *J. Med. Virol.*, 23:135–150, 1987).

There is thus a considerable body of evidence illustrating the potential value of monoclonal antibodies as agents for immune prophylaxis and therapy in HSV infection. The development of combinatorial antibody libraries displayed on the surface of phage offers the possibility of accessing monoclonal human antibody specificities against infectious agents from any individual with clearly demonstrable serum antibodies against the pathogen (Williamson, et al., *Proc. Nat'l Acad. Sci. USA*, 90:4141–4145, 1993). In the present invention, a library from a long term asymptomatic HIV-1 positive individual with serum antibody titer against HSV-1 and HSV-2 was used to isolate a diverse array of human monoclonal antibodies specific for these two viruses. The generation of panels of antibodies using this methodology permits a thorough characterization of the human antibody response to these pathogens and further identify particular antibodies of potential value for clinical applications. The present invention provides such an HSV neutralizing human antibody.

SUMMARY OF THE INVENTION

The present invention provides human monoclonal antibodies which bind and neutralize Herpes simplex virus (HSV) Type-1 and Type-2 and cell lines which produce these monoclonal antibodies. The antibodies of the invention were identified using phagemid vectors which allow identification and isolation of human monoclonal antibodies that immunoreact with HSV from combinatorial libraries. These phagemid vectors allow the rapid preparation of large numbers of neutralizing antibodies. The identified neutralizing antibodies may define new epitopes on HSV, thereby increasing the availability of new immunotherapeutic human monoclonal antibodies to HSV-associated diseases.

Also provided are amino acid sequences which confer HSV-1 and HSV-2 neutralization function to the paratope of these monoclonal antibodies and which can be used immunogenically to identify other antibodies that specifically bind and neutralize HSV. The monoclonal antibodies of the invention find particular utility as reagents for the diagnosis and immunotherapy of HSV disease.

A major advantage of the monoclonal antibodies of the invention derives from the fact that they are encoded by a human polynucleotide sequence. Thus, in vivo use of the monoclonal antibodies of the invention for diagnosis and immunotherapy of HSV disease greatly reduces the problems of significant host immune response to the passively administered antibodies which is a problem commonly encountered when monoclonal antibodies of xenogeneic or chimeric derivation are utilized.

The antibodies of the invention have extremely high neutralizing activity and may be particularly efficacious in ameliorating HSV disease when administered topically for genital, oral and ocular herpes. The ability to utilize Fab fragments in vivo for systemic protection from HSV infections provides significant advantages over the use of whole antibody molecules such as: (1) greater tissue penetration; (2) avoidance of effector functions associated with Fc, such as inflammation; and (3) rapid clearance.

In one embodiment, the invention contemplates a human monoclonal antibody capable of immunoreacting with Herpes simplex virus (HSV), and preferably neutralizes HSV. A preferred human monoclonal antibody has the binding specificity of a monoclonal antibody comprising a heavy chain immunoglobulin variable region amino acid residue sequence as found in SEQUENCE ID No. 1, and conservative substitutions thereof.

In another embodiment, the invention describes a polynucleotide sequence encoding a heavy or light chain immunoglobulin variable region amino acid residue sequence portion of a human monoclonal antibody of this invention.

Also contemplated are DNA expression vectors containing the polynucleotide, and host cells containing the vectors and polynucleotides of the invention.

The invention also contemplates a method of detecting Herpes simplex virus (HSV) comprising contacting a sample suspected of containing HSV with a diagnostically effective amount of the monoclonal antibody of this invention, and determining whether the monoclonal antibody immunoreacts with the sample. The method can be practiced in vitro or in vivo, and may include a variety of methods for determining the presence of an immunoreaction product.

In another embodiment, the invention describes a method for providing passive immunotherapy to Herpes simplex virus (HSV) disease in a human, comprising administering to the human an immunotherapeutically effective amount of the monoclonal antibody of this invention. The administration can be provided prophylactically, and by a parenteral administration. Pharmaceutical compositions containing one or more of the different human monoclonal antibodies are described for use in the therapeutic methods of the invention.

BRIEF DESCRIPTION OF THE DRAWINGS

FIG. 1 shows the neutralizing activity of Fab8, as measured by plaque reduction.

FIG. 3 shows a post-attachment neutralization assay. Fab8 reduced HSV-1 infectivity after virion attachment.

DETAILED DESCRIPTION OF THE INVENTION

Figure 1A:
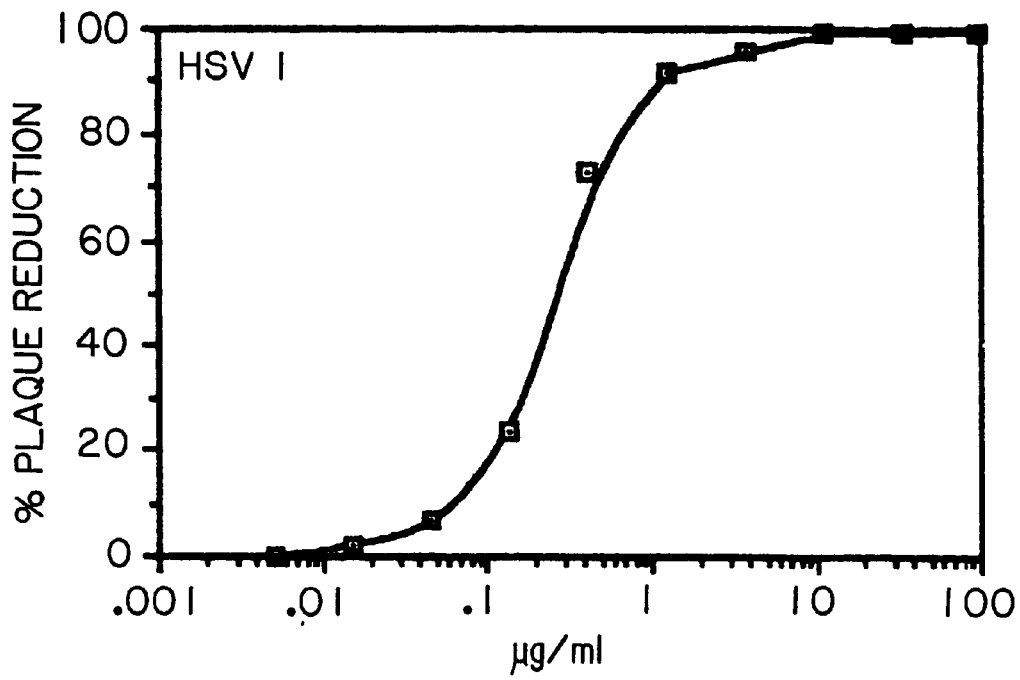
FIG. 1A shows activity against HSV-1 and FIG. 1B shows activity against HSV-2. Purified Fab8 neutralized HSV-1 with a 50% inhibition at about 0.25 $\mu$g/ml and with an 80% inhibition at 0.6 $\mu$g/ml, while HSV-2 was neutralized with a 50% inhibition at about 0.05 $\mu$g/ml and an 80% inhibition at 0.1 $\mu$g/ml.

The present invention relates to human monoclonal antibodies which are specific for, and neutralize Herpes simplex virus (HSV) Type-1 and Type-2. In a preferred embodiment of the invention, human monoclonal antibodies are disclosed which are capable of binding epitopic polypeptide sequences in glycoprotein D of HSV. Also disclosed is an antibody heavy chain amino acid sequence which is highly specific and confers neutralization of HSV when the virus is bound by antibodies having the amino acid sequence. This specificity enables the human monoclonal antibody, and human monoclonal antibodies with like specificity, to be used in the diagnosis and immunotherapy of HSV disease.

The term "HSV disease" means any disease caused, directly or indirectly, by HSV as well as diseases which predispose a patient to infection by HSV. Examples of diseases falling into the former category include genital, oral and ocular herpes. Diseases in the latter category (i.e., those which place the patient at risk of severe HSV infection) include, generally, any condition that causes a state of immunosuppression or decreased function of the immune system such as patients who receive organ transplants, AIDS patients, those with hematological or lymphoreticular neoplasms, and infants.

In one aspect, the present invention is directed to combinatorially derived human monoclonal antibodies which are reactive with and bind an HSV neutralization site and cell lines which produce such antibodies. The isolation of cell lines producing monoclonal antibodies of the invention can be accomplished using routine screening techniques which permit determination of the elementary reaction pattern of the monoclonal antibody of interest. Thus, if a human monoclonal antibody being tested binds and neutralizes members of Type-1 and Type-2 HSV in the same manner as the human monoclonal antibodies of the invention, then the human monoclonal antibody being tested and the human monoclonal antibody produced by the cell lines of the invention are equivalent.

It is also possible to determine, without undue experimentation, if a human monoclonal antibody has the same specificity as a human monoclonal antibody of the invention by ascertaining whether the former prevents the latter from binding to HSV. If the human monoclonal antibody being tested competes with the human monoclonal antibody of the invention, as shown by a decrease in binding by the human monoclonal antibody of the invention, then it is likely that the two monoclonal antibodies bind to the same, or a closely related, epitope.

Still another way to determine whether a human monoclonal antibody has the specificity of a human monoclonal antibody of the invention is to pre-incubate the human monoclonal antibody of the invention with HSV with which it is normally reactive, and then add the human monoclonal antibody being tested to determine if the human monoclonal antibody being tested is inhibited in its ability to bind HSV. If the human monoclonal antibody being tested is inhibited then, in all likelihood, it has the same, or functionally equivalent, epitopic specificity as the monoclonal antibody of the invention. Screening of human monoclonal antibodies of the invention, can be also carried out utilizing HSV and determining whether the monoclonal antibody neutralizes HSV.

By using the human monoclonal antibodies of the invention, it is now possible to produce anti-idiotypic antibodies which can be used to screen human monoclonal antibodies to identify whether the antibody has the same binding specificity as a human monoclonal antibody of the invention and also used for active immunization (Herlyn, et al., Science, 232:100, 1986). Such anti-idiotypic antibodies can be produced using well-known hybridoma techniques (Kohler and Milstein, Nature, 256:495, 1975). An anti-idiotypic antibody is an antibody which recognizes unique determinants present on the human monoclonal antibody produced by the cell line of interest. These determinants are located in the hypervariable region of the antibody. It is this region which binds to a given epitope and, thus, is responsible for the specificity of the antibody. An anti-idiotypic antibody can be prepared by immunizing an animal with the monoclonal antibody of interest. The immunized animal will recognize and respond to the idiotypic determinants of the immunizing antibody and produce an antibody to these idiotypic determinants. By using the anti-idiotypic antibodies of the immunized animal, which are specific for the human monoclonal antibody of the invention produced by a cell line which was used to immunize the second animal, it is now possible to identify other clones with the same idiotype as the antibody of the hybridoma used for immunization. Idiotypic identity between human monoclonal antibodies of two cell lines demonstrates that the two monoclonal antibodies are the same with respect to their recognition of the same epitopic determinant. Thus, by using anti-idiotypic antibodies, it is possible to identify other hybridomas expressing monoclonal antibodies having the same epitopic specificity.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody. Thus, the anti-idiotypic monoclonal antibody can be used for immunization, since the anti-idiotype monoclonal antibody binding domain effectively acts as an antigen.

The term "antibody" as used in this invention includes intact molecules as well as fragments thereof, such as Fab and F(ab')$_2$, which are capable of binding the epitopic determinant. In the present invention Fab fragments are preferred. Fabs offer several advantages over F(ab')$_2$s and whole immunoglobulin molecules as a therapeutic modality. First, because Fabs have only one binding site for their cognate antigen, the formation of immune complexes is precluded, whereas such complexes can be generated when divalent F(ab')$_2$s and whole immunoglobulin molecules encounter their target antigen. This is of some importance because immune complex deposition in tissues can produce adverse inflammatory reactions. Second, since Fabs lack an Fc region they cannot trigger adverse inflammatory reactions that are activated by Fc, such as initiation of the complement cascade. Third, the tissue penetration of the small Fab molecule is likely to be much better than that of the larger whole antibody. Fourth, Fabs can be produced easily and inexpensively in bacteria, such as *E. coli*, whereas whole immunoglobulin antibody molecules require mammalian cells for their production in useful amounts. The latter entails transfection of immunoglobulin sequences into mammalian cells with resultant transformation. Amplification of these sequences must then be achieved by rigorous selective procedures and stable transformants must be identified and maintained. The whole immunoglobulin molecules must be produced by stably transformed, high expression cells in culture with the attendant problems of serum-containing culture medium. In contrast, production of Fabs in *E. coli* eliminates these difficulties and makes it possible to produce these antibody fragments in large fermenters which are less expensive than cell culture-derived products.

In addition to Fabs, smaller antibody fragments and epitope-binding peptides having binding specificity for at least one epitope of HSV, preferably on glycoprotein D of HSV, are also contemplated by the present invention and can also be used to neutralize the virus. For example, single chain antibodies can be constructed according to the method of U.S. Pat. No. 4,946,778 to Ladner et al., which is incorporated herein by reference in its entirety. Single chain antibodies comprise the variable regions of the light and heavy chains joined by a flexible linker moiety. Yet smaller is the antibody fragment known as the single domain antibody, which comprises an isolate VH single domain. Techniques for obtaining a single domain antibody with at least some of the binding specificity of the intact antibody from which they are derived are known in the art. For instance, Ward, et al., in "Binding Activities of a Repertoire of Single Immunoglobulin Variable Domains Secreted from *Escheria coli*," Nature 341:644–646, disclose a method for screening to obtain an antibody heavy chain variable region (VH single domain antibody) with sufficient affinity for its target epitope to bind thereto in isolate form.

The monoclonal antibodies of the invention are suited for in vitro use, for example, in immunoassays in which they can be utilized in liquid phase or bound to a solid phase carrier. In addition, the monoclonal antibodies in these immunoassays can be detectably labeled in various ways. Examples of types of immunoassays which can utilize monoclonal antibodies of the invention are competitive and non-competitive immunoassays in either a direct or indirect format. Examples of such immunoassays are the radioimmunoassay (RIA) and the sandwich (immunometric) assay. Detection of the antigens using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The monoclonal antibodies of the invention can be bound to many different carriers and used to detect the presence of HSV. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, and bioluminescent compounds. Those of ordinary skill in the art will know of other suitable labels for binding to the monoclonal antibodies of the invention, or will be able to ascertain such, using routine experimentation. Furthermore, the binding of these labels to the monoclonal antibodies of the invention can be done using standard techniques common to those of ordinary skill in the art.

For purposes of the invention, HSV may be detected by the monoclonal antibodies of the invention when present in biological fluids and tissues. Any sample containing a detectable amount of HSV can be used. A sample can be a liquid such as urine, saliva, cerebrospinal fluid, blood, serum and the like, or a solid or semi-solid such as tissues, or, alternatively, a solid tissue such as those commonly used in histological diagnosis. For detection of HSV, preferred samples include a swab from a mucocutaneous lesion, a needle aspiration from a fresh vesicle, cerebrospinal fluid, brain tissue homogenate (postmortem) and urine in exceptional cases where genital herpes is complicated by urethritis or cystitis.

Another labeling technique which may result in greater sensitivity consists of coupling the antibodies to low molecular weight haptens. These haptens can then be specifically detected by means of a second reaction. For example, it is common to use haptens such as biotin, which reacts with avidin, or dinitrophenol, pyridoxal, or fluorescein, which can react with specific anti-hapten antibodies.

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

The materials for use in the assay of the invention are ideally suited for the preparation of a kit. Such a kit may comprise a carrier means being compartmentalized to receive in close confinement one or more container means such as vials, tubes, and the like, each of the container means comprising one of the separate elements to be used in the method. For example, one of the container means may comprise a human monoclonal antibody of the invention which is, or can be, detectably labelled. The kit may also have containers containing buffer(s) and/or a container comprising a reporter-means, such as a biotin-binding protein, such as avidin or streptavidin, bound to a reporter molecule, such as an enzymatic, or fluorescent label.

In using the human monoclonal antibodies of the invention for the in vivo detection of antigen, the detectably labeled monoclonal antibody is given in a dose which is diagnostically effective. The term "diagnostically effective" means that the amount of detectably labeled human monoclonal antibody is administered in sufficient quantity to enable detection of the site having the HSV antigen for which the monoclonal antibodies are specific.

The concentration of detectably labeled human monoclonal antibody which is administered should be sufficient such that the binding to HSV is detectable compared to the background. Further, it is desirable that the detectably labeled monoclonal antibody be rapidly cleared from the circulatory system in order to give the best target-to-background signal ratio.

As a rule, the dosage of detectably labeled human monoclonal antibody for in vivo diagnosis will vary depending on such factors as age, sex, and extent of disease of the individual. The dosage of human monoclonal antibody can vary from about 0.01 $mg/m^2$ to about 500 $mg/m^2$, preferably 0.1 mg/m² to about 200 mg/m², most preferably about 0.1 mg/m² to about 10 mg/m². Such dosages may vary, for example, depending on whether multiple injections are given, tissue, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 keV range, which may be readily detected by conventional gamma cameras.

For in vivo diagnosis radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, 162Dy, $^{52}$Cr, and $^{56}$Fe.

The human monoclonal antibodies of the invention can be used in vitro and in vivo to monitor the course of HSV disease therapy. Thus, for example, by measuring the increase or decrease in the number of cells infected with HSV or changes in the concentration of HSV present in the body or in various body fluids, it would be possible to determine whether a particular therapeutic regimen aimed at ameliorating the HSV disease is effective.

The human monoclonal antibodies can also be used immunotherapeutically for HSV disease. The term "immunotherapeutically" or "immunotherapy" as used herein in conjunction with the monoclonal antibodies of the invention denotes both prophylactic as well as therapeutic administration. Thus, the monoclonal antibodies can be administered to high-risk patients such as AIDS patients, in order to lessen the likelihood and/or severity of HSV disease, or administered to patients already evidencing active HSV infection.

The dosage ranges for the immunotherapeutic administration of the monoclonal antibodies of the invention are those large enough to produce the desired effect in which the symptoms of the HSV disease are ameliorated or the likelihood of infection is decreased. The dosage should not be so large as to cause adverse side effects, such as hyperviscosity syndromes, pulmonary edema, conjestive heart failure, and the like. Generally, the dosage will vary with the age, condition, sex and extent of the disease in the patient and can be determined by one of skill in the art. The dosage can be adjusted by the individual physician in the event of any complication. Dosage can vary from about 0.01 mg/kg to about 300 mg/kg, preferably from about 0.1 mg/kg to about 200 mg/kg, most preferably from about 0.2 mg/kg to about 20 mg/kg, in one or more dose administrations daily, for one or several days. Preferred is administration of the antibody for 2 to 5 or more consecutive days in order to avoid "rebound" of virus replication from occurring.

The human monoclonal antibodies of the invention can be administered parenterally by injection or by gradual infusion over time. The human monoclonal antibodies of the invention can be administered intravenously, intraperitoneally, intramuscularly, subcutaneously, or intracavity. A formulation containing the monoclonal antibodies of the invention may also be administered externally to a subject, at the site of the disease for exertion of local or transdermal action. When used therapeutically, a preferred route of administration of the human monoclonal antibodies of the invention is by topical adminstration, especially directly to the virally induced lesion. Techniques for preparing topical or transdermal delivery systems containing the antibody of the invention are well known those of skill in the art.

Generally, such systems should utilize components which will not significantly impair the biological properties of the antibody, such as the paratope binding capacity (see, for example, Sciarra and Cutie, Aerosols, in Remington Pharmaceutical Sciences, 18th edition, 1990, pp 1694–1712; incorporated by reference). Those of skill in the art can readily determine the various parameters and conditions for producing antibody-containing compositions without resort to undue experimentation. Topical compositions include various known mixtures which may be applied topically and which allow even spreading of the active ingredient over the affected area. Accordingly, such topical compositions include those pharmaceutically acceptable forms in which the compound is applied externally by direct contact with the skin surface to be treated. Examples of such conventional pharmaceutical forms of topical formulations include creams, lotions, solutions, gels, ointments and unguents. The formulation may optionally contain additional agents other than the ones of the invention, which are biologically active or inactive. Such inactive agents include surfactants, humectants, wetting agents, emulsifiers, and propellants that allow even spreading over the affected area.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The invention also relates to a method for preparing a medicament or pharmaceutical composition comprising the human monoclonal antibodies of the invention, the medicament being used for immunotherapy of HSV disease.

A preferred embodiment of the invention relates to human monoclonal antibodies which neutralize both HSV-1 and -2 whose heavy chains comprise in CDR3 the polypeptide VAYMLEPTVTAGGLDV (SEQUENCE ID No. 1), and conservative variations of the peptide.

The amino acid sequence of the entire variable region of the heavy chain of the antibody of the invention is shown in SEQUENCE ID No. 2. Also encompassed by the present invention are certain amino acid sequences that bind to epitopic sequences in glycoprotein D of HSV and confer neutralization of HSV when bound thereto. The term "conservative variation" or "substitution" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies having the substituted polypeptide also neutralize HSV. Analogously, another preferred embodiment of the invention relates to polynucleotides which encode the above noted heavy chain polypeptide and to polynucleotide sequences which are complementary to these polynucleotide sequences. Complementary polynucleotide sequences include those sequences which hybridize to the polynucleotide sequences of the invention under stringent hybridization conditions.

The present invention describes methods for producing novel HSV-neutralizing human monoclonal antibodies. The methods are based generally on the use of combinatorial libraries of antibody molecules which can be produced from a variety of sources, and include naive libraries, modified libraries, and libraries produced directly from human donors exhibiting an HSV-specific immune response.

The combinatorial library production and manipulation methods have been extensively described in the literature, and will not be reviewed in detail herein, except for those feature required to make and use unique embodiments of the present invention. However, the methods generally involve the use of a filamentous phage (phagemid) surface expression vector system for cloning and expressing antibody species of the library. Various phagemid cloning systems to produce combinatorial libraries have been described by others. See, for example the preparation of combinatorial antibody libraries on phagemids as described by Kang, et al., *Proc. Natl. Acad. Sci., USA*, 88:4363–4366 (1991); Barbas, et al., *Proc. Natl. Acad. Sci., USA*, 88:7978–7982 (1991); Zebedee, et al., *Proc. Natl. Acad. Sci., USA*, 89:3175–3179 (1992); Kang, et al., *Proc. Natl. Acad. Sci., USA*, 88:11120–11123 (1991); Barbas, et al., *Proc. Natl. Acad. Sci., USA*, 89:4457–4461 (1992); and Gram, et al., *Proc. Natl. Acad. Sci., USA*, 89:3576–3580 (1992), which references are hereby incorporated by reference.

In one embodiment, the method involves preparing a phagemid library of human monoclonal antibodies by using donor immune cell messenger RNA from HSV-infected donors. The donors can be symptomatic of a HSV infection, but the donor can also be asymptomatic, as the resulting library contains a substantially higher number of HSV-neutralizing human monoclonal antibodies. Additionally, because HSV infection is often associated with other diseases, the patient may optionally present substantial symptoms of one or more other diseases typically associated with symptomatic or asymptomatic HSV infection, notably AIDS, as demonstrated by the library utilized herein.

In another embodiment, the donor is naive relative to a conventional immune response to HSV, i.e., the donor is not HSV-infected, and yet antibodies in the donor cross-react with one or more HSV antigens. Alternatively, the library can be synthetic, or can be derived from a donor who has an immune response to other antigens.

The method for producing a human monoclonal antibody generally involves (1) preparing separate H and L chain-encoding gene libraries in cloning vectors using human immunoglobulin genes as a source for the libraries, (2) combining the H and L chain encoding gene libraries into a single dicistronic expression vector capable of expressing and assembling a heterodimeric antibody molecule, (3) expressing the assembled heterodimeric antibody molecule on the surface of a filamentous phage particle, (4) isolating the surface-expressed phage particle using immunoaffinity techniques such as panning of phage particles against a preselected antigen, thereby isolating one or more species of phagemid containing particular H and L chain-encoding genes and antibody molecules that immunoreact with the preselected antigen.

As described herein the Examples, the resulting phagemid library can be manipulated to increase and/or alter the immunospecificities of the monoclonal antibodies of the library to produce and subsequently identify additional, desirable, human monoclonal antibodies of the present invention. For example, the heavy (H) chain and light (L) chain immunoglobulin molecule encoding genes can be randomly mixed (shuffled) to create new HL pairs in an assembled immunoglobulin molecule. Additionally, either or both the H and L chain encoding genes can be mutagenized in a complementarity determining region (CDR) of the variable region of the immunoglobulin polypeptide, and subsequently screened for desirable immunoreaction and neutralization capabilities.

In one embodiment, the H and L genes can be cloned into separate, monocistronic expression vectors, referred to as a "binary" system described further herein. In this method, step (2) above differs in that the combining of H and L chain encoding genes occurs by the co-introduction of the two binary plasmids into a single host cell for expression and assembly of a phagemid having the surface accessible antibody heterodimer molecule.

In one shuffling embodiment, the shuffling can be accomplished with the binary expression vectors, each capable of expressing a single heavy or light chain encoding gene.

In the present methods, the antibody molecules are monoclonal because the cloning methods allow for the preparation of clonally pure species of antibody producing cell lines. In addition, the monoclonal antibodies are human because the H and L chain encoding genes are derived from human immunoglobulin producing immune cells, such as spleen, thymus, bone marrow, and the like.

In a method for producing a HSV-neutralizing human monoclonal antibody, it is also required that the resulting antibody library, immunoreactive with a preselected HSV antigen, be additionally screened for the presence of antibody species which have the capacity to neutralize HSV in one or more of the assays described herein for determining neutralization capacity. Thus, a preferred library of antibody molecules is first produced which binds to an HSV antigen, and then is screened for the presence of HSV-neutralizing antibodies as described herein. Additional libraries can be screened from shuffled libraries for additional HSV-immunoreactive and neutralizing human monoclonal antibodies.

As a further characterization of the present invention the nucleotide and corresponding amino acid residue sequence of the antibody molecule's H or L chain encoding gene is determined by nucleic acid sequencing. The primary amino acid residue sequence information provides essential information regarding the antibody molecule's epitope reactivity.

Sequence comparisons of identified HSV-immunoreactive monoclonal antibody variable chain region sequences are aligned based on sequence homology, and groups of related antibody molecules are identified in which heavy chain or light chain genes share substantial sequence homology.

An exemplary preparation of a human monoclonal antibody is described in the Examples. The isolation of a particular vector capable of expressing an antibody of interest involves the introduction of the dicistronic expression vector into a host cell permissive for expression of filamentous phage genes and the assembly of phage particles. Where the binary vector system is used, both vectors are introduced in the host cell. Typically, the host is *E. coli*. Thereafter, a helper phage genome is introduced into the host cell containing the immunoglobulin expression vector(s) to provide the genetic complementation necessary to allow phage particles to be assembled. The resulting host cell is cultured to allow the introduced phage genes and immunoglobulin genes to be expressed, and for phage particles to be assembled and shed from the host cell. The shed phage particles are then harvested (collected) from the host cell culture media and screened for desirable immunoreaction and neutralization properties. Typically, the harvested particles are "panned" for immunoreaction with a preselected antigen. For example, the preselected antigen, such as a virus, can be attached directly to a solid phase or indirectly to a solid phase via an antibody specific for the antigen wherein the antibody is first attached to the solid phase before the particles are panned. The strongly immunoreactive particles are then collected, and individual species of particles are clonally isolated and further screened for HSV neutralization. Phage which produce neutralizing antibodies are selected and used as a source of a human HSV neutralizing monoclonal antibody of this invention.

Human monoclonal antibodies of this invention can also be produced by altering the nucleotide sequence of a polynucleotide sequence that encodes a heavy or light chain of a monoclonal antibody of this invention. For example, by site directed mutagenesis, one can alter the nucleotide sequence of an expression vector and thereby introduce changes in the resulting expressed amino acid residue sequence. One can take a known polynucleotide and randomly after it by random mutagenesis, reintroduce the altered polynucleotide into an expression system and subsequently screen the product H:L pair for HSV-neutralizing activity.

Site-directed and random mutagenesis methods are well known in the polynucleotide arts, and are not to be construed as limiting as methods for altering the nucleotide sequence of a subject polynucleotide.

Because an immunoaffinity isolated antibody composition includes phage particles containing surface antibody, one embodiment involves the manipulation of the resulting cloned genes to truncate the immunoglobulin-coding gene such that a soluble Fab fragment is secreted by the host *E. coli* cell containing the phagemid vector rather than the production of a phagemid having surface antibody. Thus, the resulting manipulated cloned immunoglobulin genes produce a soluble Fab which can be readily characterized in ELISA assays for epitope binding studies, in competition assays with known anti-HSV antibody molecules, and in HSV neutralization assays. The solubilized Fab provides a reproducible and comparable antibody preparation for comparative and characterization studies.

The preparation of soluble Fab is generally described in the immunological arts, and can be conducted as described herein in the Examples, or as described by Burton, et al., *Proc. Natl. Acad. Sci., USA*, 88:10134–10137 (1991). The preparation of human monoclonal antibodies of this invention depends, in one embodiment, on the cloning and expression vectors used to prepare the combinatorial antibody libraries described herein. The cloned immunoglobulin heavy and light chain genes can be shuttled between lambda vectors, phagemid vectors and plasmid vectors at various stages of the methods described herein.

The phagemid vectors produce fusion proteins that are expressed on the surface of an assembled filamentous phage particle. A preferred phagemid vector of the present invention is a recombinant DNA (rDNA) molecule containing a nucleotide sequence that codes for and is capable of expressing a fusion polypeptide containing, in the direction of amino- to carboxy-terminus, (1) a prokaryotic secretion signal domain, (2) a heterologous polypeptide defining an immunoglobulin heavy or light chain variable region, and (3) a filamentous phage membrane anchor domain. The vector includes DNA expression control sequences for expressing the fusion polypeptide, preferably prokaryotic control sequences.

The filamentous phage membrane anchor is preferably a domain of the cpIII or cpVIII coat protein capable of associating with the matrix of a filamentous phage particle, thereby incorporating the fusion polypeptide onto the phage surface. The secretion signal is a leader peptide domain of a protein that targets the protein to the periplasmic membrane of gram negative bacteria. A preferred secretion signal is a pelB secretion signal. The predicted amino acid residue sequences of the secretion signal domain from two pelB gene product variants from *Erwinia carotova* are described in Lei, et al., *Nature*, 331:543–546 (1988).

The leader sequence of the pelB protein has previously been used as a secretion signal for fusion proteins. Better, et al., *Science*, 240:1041–1043 (1988); Sastry, et al., *Proc. Nat. Acad. Sci., USA*, 86:5728–5732 (1989); and Mullinax, et al., *Proc. Natl. Acad. Sci., USA*, 87:8095–8099 (1990). Amino add residue sequences for other secretion signal polypeptide domains from *E. coli* useful in this invention as described in Oliver, *Escherichia coli* and *Salmonella typhimurium*, Neidhard, F. C. (ed.), American Society for Microbiology, Washington, D.C., 1:56–69 (1987).

Preferred membrane anchors for the vector are obtainable from filamentous phage M13, f1, fd, and equivalent filamentous phage. Preferred membrane anchor domains are found in the coat proteins encoded by gene III and gene VIII. The membrane anchor domain of a filamentous phage coat protein is a portion of the carboxy terminal region of the coat protein and includes a region of hydrophobic amino acid residues for spanning a lipid bilayer membrane, and a region of charged amino add residues normally found at the cytoplasmic face of the membrane and extending away from the membrane.

In the phage f1, gene VIII coat protein's membrane spanning region comprises residue Trp-26 through Lys-40, and the cytoplasmic region comprises the carboxy-terminal 11 residues from 41 to 52 (Ohkawa, et al., *J. Biol. Chem.*, 256:9951–9958 (1981)). An exemplary membrane anchor would consist of residues 26 to 40 of cpVIII. Thus, the amino add residue sequence of a preferred membrane anchor domain is derived from the M13 filamentous phage gene VIII coat protein (also designated cpVIII or CP 8). Gene VIII coat protein is present on a mature filamentous phage over the majority of the phage particle with typically about 2500 to 3000 copies of the coat protein.

In addition, the amino acid residue sequence of another preferred membrane anchor domain is derived from the M13 filamentous phage gene III coat protein (also designated cpIII). Gene III coat protein is present on a mature filamentous phage at one end of the phage particle with typically about 4 to 6 copies of the coat protein.

For detailed descriptions of the structure of filamentous phage particles, their coat proteins and particle assembly, see the reviews by Rached, et al., *Microbiol. Rev.*, 50:401–427 (1986); and Model, et al., in "The Bacteriophages: Vol. 2", R. Calendar, ed. Plenum Publishing Co., pp. 375–456 (1988).

DNA expression control sequences comprise a set of DNA expression signals for expressing a structural gene product and include both 5' and 3' elements, as is well known, operatively linked to the cistron such that the cistron is able to express a structural gene product. The 5' control sequences define a promoter for initiating transcription and a ribosome binding site operatively linked at the 5' terminus of the upstream translatable DNA sequence.

To achieve high levels of gene expression in *E. coli*, it is necessary to use not only strong promoters to generate large quantities of mRNA, but also ribosome binding sites to ensure that the mRNA is efficiently translated. In *E. coli*, the ribosome binding site includes an initiation codon (AUG) and a sequence 3–9 nucleotides long located 3–11 nucleotides upstream from the initiation codon (Shine, et al., *Nature*, 254:34 (1975). The sequence, AGGAGGU, which is called the Shine-Dalgarno (SD) sequence, is complementary to the 3' end of *E. coil* 16S rRNA. Binding of the ribosome to mRNA and the sequence at the 3' end of the mRNA can be affected by several factors:

(i) The degree of complementarity between the SD sequence and 3' end of the 16S rRNA.

(ii) The spacing and possibly the DNA sequence lying between the SD sequence and the AUG. Roberts, et al., *Proc. Natl. Acad. Sci., USA*, 76:760, (1979a); Roberts, et al., *Proc. Natl. Acad. Sci. USA*, 76:5596 (1979b); Guarente, et al., *Science*, 209:1428 (1980); and Guarente, et al., *Cell*, 20:543 (1980). Optimization is achieved by measuring the level of expression of genes in plasmids in which this spacing is systematically aftered. Comparison of different mRNAs shows that there are statistically preferred sequences from positions −20 to +13 (where the A of the AUG is position 0). Gold, et al., *Annu. Rev. Microbiol.*, 35:365 (1981). Leader sequences have been shown to influence translation dramatically. Roberts, et al., 1979 a, b supra.

(iii) The nucleotide sequence following the AUG, which affects ribosome binding. Taniguchi, et al., *J. Mol. Biol.*, 118:533 (1978). The 3' control sequences define at least one termination (stop) codon in frame with and operatively linked to the heterologous fusion polypeptide.

In preferred embodiments, the vector utilized includes a prokaryotic origin of replication or replicon, i.e., a DNA sequence having the ability to direct autonomous replication and maintenance of the recombinant DNA molecule extra chromosomally in a prokaryotic host cell, such as a bacterial host cell, transformed therewith. Such origins of replication are well known in the art. Preferred origins of replication are those that are efficient in the host organism. A preferred host cell is *E. coli*. For use of a vector in *E. coli*, a preferred origin of replication is ColE1 found in pBR322 and a variety of other common plasmids. Also preferred is the p15A origin of replication found on pACYC and its derivatives. The ColE1 and p15A replicon have been extensively utilized in molecular biology, are available on a variety of plasmids and are described at least by Sambrook, et al., in "Molecular Cloning: a Laboratory Manual", 2nd edition, Cold Spring Harbor Laboratory Press (1989).

The ColE1 and p15A replicons are particularly preferred for use in one embodiment of the present invention where two "binary" plasmids are utilized because they each have the ability to direct the replication of plasmid in *E. coil* while the other replicon is present in a second plasmid in the same *E. coli* cell.

In other words, ColE1 and p15A are non-interfering replicons that allow the maintenance of two plasmids in the same host (see, for example, Sambrook, et al., supar, at pages 1.3–1.4). This feature is particularly important in the binary vectors embodiment of the present invention because a single host cell permissive for phage replication must support the independent and simultaneous replication of two separate vectors, namely a first vector for expressing a heavy chain polypeptide, and a second vector for expressing a light chain polypeptide.

In addition, those embodiments that include a prokaryotic replicon can also include a gene whose expression confers a selective advantage, such as drug resistance, to a bacterial host transformed therewith. Typical bacterial drug resistance genes are those that confer resistance to ampicillin, tetracycline, neomycin/kanamycin or cholamphenicol. Vectors typically also contain convenient restriction sites for insertion of translatable DNA sequences. Exemplary vectors are the plasmids pUC8, pUC9, pBR322, and pBR329 available from BioRad Laboratories, (Richmond, Calif.) and pPL and pKK223 available from Pharmacia, (Piscataway, N.J.).

A vector for expression of a monoclonal antibody of the invention on the surface of a filamentous phage particle is a recombinant DNA (rDNA) molecule adapted for receiving and expressing translatable first and second DNA sequences in the form of first and second polypeptides wherein one of the polypeptides is fused to a filamentous phage coat protein membrane anchor. That is, at least one of the polypeptides is a fusion polypeptide containing a filamentous phage membrane anchor domain, a prokaryotic secretion signal domain, and an immunoglobulin heavy or light chain variable domain.

A DNA expression vector for expressing a heterodimeric antibody molecule provides a system for independently cloning (inserting) the two translatable DNA sequences into two separate cassettes present in the vector, to form two separate cistrons for expressing the first and second polypeptides of the antibody molecule, or the ligand binding portions of the polypeptides that comprise the antibody molecule (i.e., the H and L variable regions of an immunoglobulin molecule). The DNA expression vector for expressing two cistrons is referred to as a dicistronic expression vector.

The vector comprises a first cassette that includes upstream and downstream translatable DNA sequences operatively linked via a sequence of nucleotides adapted for directional ligation to an insert DNA. The upstream translatable sequence encodes the secretion signal as defined herein. The downstream translatable sequence encodes the filamentous phage membrane anchor as defined herein. The cassette preferably includes DNA expression control sequences for expressing the receptor polypeptide that is produced when an insert translatable DNA sequence (insert DNA) is directionally inserted into the cassette via the sequence of nucleotides adapted for directional ligation. The filamentous phage membrane anchor is preferably a domain of the cpIII or cpVIII coat protein capable of binding the matrix of a filamentous phage particle, thereby incorporating the fusion polypeptide onto the phage surface.

The receptor expressing vector also contains a second cassette for expressing a second receptor polypeptide. The second cassette includes a second translatable DNA sequence that encodes a secretion signal, as defined herein, operatively linked at its 3' terminus via a sequence of nucleotides adapted for directional ligation to a downstream DNA sequence of the vector that typically defines at least one stop codon in the reading frame of the cassette. The second translatable DNA sequence is operatively linked at its 5' terminus to DNA expression control sequences forming the 5' elements. The second cassette is capable, upon insertion of a translatable DNA sequence (insert DNA), of expressing the second fusion polypeptide comprising a receptor of the secretion signal with a polypeptide coded by the insert DNA.

An upstream translatable DNA sequence encodes a prokaryotic secretion signal as described earlier. The upstream translatable DNA sequence encoding the pelB secretion signal is a preferred DNA sequence for inclusion in a receptor expression vector. A downstream translatable DNA sequence encodes a filamentous phage membrane anchor as described earlier. Thus, a downstream translatable DNA sequence encodes an amino acid residue sequence that corresponds, and preferably is identical, to the membrane anchor domain of either a filamentous phage gene III or gene VIII coat polypeptide.

A cassette in a DNA expression vector of this invention is the region of the vector that forms, upon insertion of a translatable DNA sequence (insert DNA), a sequence of nucleotides capable of expressing, in an appropriate host, a fusion polypeptide. The expression-competent sequence of nucleotides is referred to as a cistron. Thus, the cassette comprises DNA expression control elements operatively linked to the upstream and downstream translatable DNA sequences. A cistron is formed when a translatable DNA sequence is directionally inserted (directionally ligated) between the upstream and downstream sequences via the sequence of nucleotides adapted for that purpose. The resulting three translatable DNA sequences, namely the upstream, the inserted and the downstream sequences, are all operatively linked in the same reading frame.

Thus, a DNA expression vector for expressing an antibody molecule provides a system for cloning translatable DNA sequences into the cassette portions of the vector to produce cistrons capable of expressing the first and second polypeptides, i.e., the heavy and light chains of a monoclonal antibody.

As used herein, the term "vector" refers to a nucleic acid molecule capable of transporting between different genetic environments another nucleic acid to which it has been operatively linked. Preferred vectors are those capable of autonomous replication and expression of structural gene products present in the DNA segments to which they are operatively linked. Vectors, therefore, preferably contain the replicons and selectable markers described earlier.

As used herein with regard to DNA sequences or segments, the phrase "operatively linked" means the sequences or segments have been covalently joined, preferably by conventional phosphodiester bonds, into one strand of DNA, whether in single or double stranded form. The choice of vector to which transcription unit or a cassette of this invention is operatively linked depends directly, as is well known in the art, on the functional properties desired, e.g., vector replication and protein expression, and the host cell to be transformed, these being limitations inherent in the art of constructing recombinant DNA molecules.

A sequence of nucleotides adapted for directional ligation, i.e., a polylinker, is a region of the DNA expression vector that (1) operatively links for replication and transport the upstream and downstream translatable DNA sequences and (2) provides a site or means for directional ligation of a DNA sequence into the vector. Typically, a directional polylinker is a sequence of nucleotides that defines two or more restriction endonuclease recognition sequences, or restriction sites. Upon restriction cleavage, the two sites yield cohesive termini to which a translatable DNA sequence can be ligated to the DNA expression vector. Preferably, the two restriction sites provide, upon restriction cleavage, cohesive termini that are non-complementary and thereby permit directional insertion of a translatable DNA sequence into the cassette. In one embodi- ment, the directional ligation means is provided by nucleotides present in the upstream translatable DNA sequence, downstream translatable DNA sequence, or both. In another embodiment, the sequence of nucleotides adapted for directional ligation comprises a sequence of nucleotides that defines multiple directional cloning means. Where the sequence of nucleotides adapted for directional ligation defines numerous restriction sites, it is referred to as a multiple cloning site.

In a preferred embodiment, a DNA expression vector is designed for convenient manipulation in the form of a filamentous phage particle encapsulating a genome according to the teachings of the present invention. In this embodiment, a DNA expression vector further contains a nucleotide sequence that defines a filamentous phage origin of replication such that the vector, upon presentation of the appropriate genetic complementation, can replicate as a filamentous phage in single stranded replicative form and be packaged into filamentous phage particles. This feature provides the ability of the DNA expression vector to be packaged into phage particles for subsequent segregation of the particle, and vector contained therein, away from other particles that comprise a population of phage particles.

A filamentous phage origin of replication is a region of the phage genome, as is well known, that defines sites for initiation of replication, termination of replication and packaging of the replicative form produced by replication (see, for example, Rasched, et al., *Microbiol. Rev.*, 50:401–427 (1986); and Horiuchi, *J. Mol. Biol.*, 188:215–223 (1986)).

A preferred filamentous phage origin of replication for use in the present invention is an M13, f1 or fd phage origin of replication (Short, et al., *Nucl. Acids Res.*, 16:7583–7600 (1988)). Preferred DNA expression vectors for cloning and expression a human monoclonal antibody of this invention are the dicistronic expression vectors pCOMB8, pCOMB2-8, pCOMB3, pCOMB2-3 and pCOMB2-3', described herein.

A particularly preferred vector of the present invention includes a polynucleotide sequence that encodes a heavy or light chain variable region of a human monoclonal antibody of the present invention. Particularly preferred are vectors that include a nucleotide sequence that encodes a heavy chain CDR3 amino acid residue sequence shown in SEQUENCE ID No.1 that encodes a heavy chain having the binding specificity of those sequences shown in SEQUENCE ID No. 1 or that encodes a heavy chain CDR3 region having conservative substitutions relative to a sequence shown in SEQUENCE ID No. 1, and complementary polynucleotide sequences thereto. The entire heavy chain amino acid residue sequence for the preferred antibody of the invention is shown in SEQUENCE ID No. 2.

Insofar as polynucleotides are component parts of a DNA expression vector for producing a human monoclonal antibody heavy or light chain immunoglobulin variable region amino acid residue sequence, the invention also contemplates isolated polynucleotides that encode such heavy or light chain sequences.

It is to be understood that, due to the genetic code and its attendant redundancies, numerous polynucleotide sequences can be designed that encode a contemplated heavy or light chain immunoglobulin variable region amino acid residue sequence. Thus, the invention contemplates such alternate polynucleotide sequences incorporating the features of the redundancy of the genetic code.

Insofar as the expression vector for producing a human monoclonal antibody of this invention is carried in a host cell compatible with expression of the antibody, the invention contemplates a host cell containing a vector or polynucleotide of this invention. A preferred host cell is $E.\ coli$, as described herein.

An $E.\ coli$ culture containing a preferred expression vector that produces a human monoclonal antibody of this invention was deposited pursuant to Budapest Treaty requirements with the American Type Culture Collection (ATCC), Rockville, Md., as described herein.

The invention now being fully described, it will be apparent to one of ordinary skill in the art that various changes and modifications can be made without departing from the spirit or scope of the invention.

EXAMPLE 1

CONSTRUCTION OF A DICISTRONIC EXPRESSION VECTOR FOR PRODUCING A HETERODIMERIC RECEPTOR ON PHAGE PARTICLES

To obtain a vector system for generating a large number of Fab antibody fragments that can be screened directly, expression libraries in bacteriophage Lambda have previously been constructed as described in Huse, et al (*Science*, 246:1275–1281, 1989). However, these systems did not contain design features that provide for the expressed Fab to be targeted to the surface of a filamentous phage particle as described by Barbas, et al (*Proc. Natl. Acad. Sci. USA*, 33:7978–7982, 1991).

The main criterion used in choosing a vector system was the necessity of generating the largest number of Fab fragments which could be screened directly. Bacteriophage Lambda was selected as the starting point to develop an expression vector for three reasons. First, in vitro packaging of phage DNA was the most efficient method of reintroducing DNA into host cells. Second, it was possible to detect protein expression at the level of single phage plaques. Finally, the screening of phage libraries typically involved less difficulty with nonspecific binding. The alternative, plasmid cloning vectors, are only advantageous in the analysis of clones after they have been identified. This advantage was not lost in the present system because of the use of a dicistronic expression vector such as pCombVIII, thereby permitting a plasmid containing the heavy chain, light chain, or Fab expressing inserts to be excised.

a. Construction of Dicistronic Expression Vector pCOMB (i) Preparation of Lambda Zap™ II Lambda Zap™ II is a derivative of the original Lambda Zap (ATCC #40,298) that maintains all of the characteristics of the original Lambda Zap including 6 unique cloning sites, fusion protein expression, and the ability to rapidly excise the insert in the form of a phagemid (Bluescript SK-), but lacks the SAM 100 mutation, allowing growth on many Non-Sup F strains, including XL1-Blue. The Lambda Zaps™ II was constructed as described in Short, et al., (*Nuc. Acids Res.*, 16:7583–7600, 1988), by replacing the lambda S gene contained in a 4254 base pair (bp) DNA fragment produced by digesting lambda Zap with the restriction enzyme Nco I. This 4254 bp DNA fragment was replaced with the 4254 bp DNA fragment containing the Lambda S gene isolated from Lambda gt10 (ATCC #40,179) after digesting the vector with the restriction enzyme Nco I. The 4254 bp DNA fragment isolated from lambda gt10 was ligated into the original lambda Zap vector using T4 DNA ligase and standard protocols such as those described in *Current Protocols in Molecular Biology*, Ausubel, et al., eds., John Wiley and Sons, N.Y., 1987, to form Lambda Zap™ II.

(ii) Preparation of Lambda Hc2

To express a plurality of $V_H$-coding DNA homologs in an $E.\ coli$ host cell, a vector designated Lambda Hc2 was constructed. The vector provided the following: the capacity to place the $V_H$-coding DNA homologs in the proper reading frame; a ribosome binding site as described by Shine, et al., (*Nature*, 254:34, 1975); a leader sequence directing the expressed protein to the periplasmic space designated the pelB secretion signal; a polynucleotide sequence that coded for a known epitope (epitope tag); and also a polynucleotide that coded for a spacer protein between the $V_H$-coding DNA homolog and the polynucleotide coding for the epitope tag. Lambda Hc2 has been previously described by Huse, et al., (*Science*, 246:1274–1281, 1989).

To prepare Lambda Hc2, a synthetic DNA sequence containing all of the above features was constructed by designing single stranded polynucleotide segments of 20–40 bases that would hybridize to each other and form the double stranded synthetic DNA sequence. The individual single-stranded polynucleotide segments are shown in Table 1.

Polynucleotides N2, N3, N9-4, N11, N10-5, N6, N7 and N8 (Table 1) were kinased by adding 1 µl of each polynucleotide (0.1 µg/µl) and 20 units of $T_4$ polynucleotide kinase to a solution containing 70 mM Tris-HCl, pH 7.6, 10 mM $MgCl_2$, 5 mM dithiothreitol (DTT), 10 mM beta-mercaptoethanol, 500 micro-grams per milliliter µg/ml) bovine serum albumin (BSA). The solution was maintained at 37 degrees Centigrade (37° C.) for 30 minutes and the reaction stopped by maintaining the solution at 65° C. for 10 minutes. The two end polynucleotides, 20 mg of polynucleotides N1 and polynucleotides N12, were added to the above kinasing reaction solution together with 1/10 volume of a solution containing 20.0 mM Tris-HCl, pH 7.4, 2.0 mM $MgCl_2$ and 50.0 mM NaCl. This solution was heated to 70° C. for 5 minutes and allowed to cool to room temperature, approximately 25° C., over 1.5 hours in a 500 ml beaker of water. During this time period all 10 polynucleotides annealed to form a double stranded synthetic DNA insert. The individual polynucleotides were covalently linked to each other to stabilize the synthetic DNA insert by adding 40 µl of the above reaction to a solution containing 50 mM Tris-HCl, pH 7.5, 7 mM $MgCl_2$, 1 mM DTT, 1 mM adenosine triphosphate (ATP) and 10 units of T4 DNA ligase. This solution was maintained at 37° C. for 30 minutes and then the T4 DNA ligase was inactivated by maintaining the solution at 65° C. for 10 minutes. The end polynucleotides were kinased by mixing 52 µl of the above reaction, 4 µl of a solution containing 10 mM ATP and 5 units of T4 polynucleotide kinase. This solution was maintained at 37° C. for 30 minutes and then the T4 polynucleotide kinase was inactivated by maintaining the solution at 65° C. for 10 minutes.

TABLE 1

| N1) | 5' GGCCGCAAATTCTATTTCAAGGAGACAGTCAT 3'<br>(SEQUENCE ID NO. 3) |
|---|---|
| N2) | 5' AATGAAATACCTATTGCCTACGGCAGCCGCTGGATT 3'<br>(SEQUENCE ID NO. 4) |
| N3) | 5' GTTATTACTCGCTGCCCAACCAGCCATGGCCC 3'<br>(SEQUENCE ID NO. 5) |
| N6) | 5' CAGTTTCACCTGGGCCATGGCTGGTTGGG 3'<br>(SEQUENCE ID NO. 6) |
| N7) | 5'CAGCGAGTAATAACAATCCAGCGGCTGCCGTAGGCAATAG3'<br>(SEQUENCE ID NO. 7) |
| N8) | 5' GTATTTCATTATGACTGTCTCCTTGAAATAGAATTTGC 3'<br>(SEQUENCE ID NO. 8) |
| N9-4) | 5'AGGTGAAACTGCTCGAGATTTCTAGACTAGTTACCCGTAC3'<br>(SEQUENCE ID NO. 9) |
| N10-5) | 5' CGGAACGTCGTACGGGTAACTAGTCTAGAAATCTCGAG 3'<br>(SEQUENCE ID NO. 10) |
| N11) | 5' GACGTTCCGGACTACGGTTCTTAATAGAATTCG 3'<br>(SEQUENCE ID NO. 11) |
| N12) | 5' TCGACGAATTCTATTAAGAACCGTAGTC 3'<br>(SEQUENCE ID NO. 12) |

The completed synthetic DNA insert was ligated directly into the Lambda Zap™ II vector described in Example 1 a(i) that had been previously digested with the restriction enzymes, Not I and Xho I. The ligation mixture was packaged according to the manufacture's instructions using Gigapack II Gold packing extract available from Stratagene, La Jolla, Calif. The packaged ligation mixture was plated on XL1-Blue cells (Stratagene). Individual Lambda plaques were cored and the inserts excised according to the in vivo excision protocol for Lambda Zap™ II provided by the manufacturer (Stratagene). This in vivo excision protocol moved the cloned insert from the Lambda Hc2 vector into a phagemid vector to allow for easy manipulation and sequencing. The accuracy of the above cloning steps was confirmed by sequencing the insert using the Sanger dideoxy method described in by Sanger, et al., (*Proc. Natl. Aced. Sci. USA*, 74:5463–5467, 1977), and using the manufacture's instructions in the AMV Reverse Transcriptase $^{35}$S-ATP sequencing kit (Stratagene).

(iii) Preparation of Lambda Lc2

To express a plurality of $V_L$-coding DNA homologs in an *E.coli* host cell, a vector designated Lambda Lc2 was constructed having the capacity to place the $V_L$-coding DNA homologs in the proper reading frame, provided a ribosome binding site as described by Shine, et al., (*Nature*, 254:34, 1975), provided the pelB gene leader sequence secretion signal that has been previously used to successfully secrete Fab fragments in *E. coli* by Lei, et aL (J. Bac., 169:4379, 1987) and Better, et al., (*Science*, 240: 1041, 1988), and also provided a polynucleotide containing a restriction endonuclease site for cloning. Lambda Lc2 has been previously described by Huse, et al., (*Science*, 246:1275–1281, 1989).

A synthetic DNA sequence containing all of the above features was constructed by designing single stranded polynucleotide segments of 20–60 bases that would hybridize to each other and form the double stranded synthetic DNA. The sequence of each individual single-stranded polynucleotide segment (1–8) within the double stranded synthetic DNA sequence is shown in Table 2.

Polynucleotides shown in Table 2 were kinased by adding 1 µl (0.1 µg/µl) of each polynucleotide and 20 units of $T_4$ polynucleotide kinase to a solution containing 70 mM Tris-HCl, pH 7.6, 10 mM MgCl, 5 mM DTT, 10 mM beta-mercaptoethanol, 500 mg/ml of BSA. The solution was maintained at 37° C. for 30 minutes and the reaction stopped by maintaining the solution at 65° C. for 10 minutes. The 20 ng each of the two end polynucleotides, 01 and 08, were added to the above kinasing reaction solution together with 1/10 volume of a solution containing 20.0 mM Tris-HCl, pH 7.4, 2.0 mM MgCl and 15.0 mM sodium chloride (NaCl). This solution was heated to 70° C. for 5 minutes and allowed to cool to room temperature, approximately 25° C., over 1.5 hours in a 500 ml beaker of water. During this time period all 8 polynucleotides annealed to form the double stranded synthetic DNA insert shown in FIG. 3. The individual polynucleotides were covalently linked to each other to stabilize the synthetic DNA insert by adding 40 µl of the above reaction to a solution containing 50 ml Tris-HCl, pH 7.5, 7 ml MgCl, 1 mm DTT, 1 mm ATP and 10 units of T4 DNA ligase. This solution was maintained at 37° C. for 30 minutes and then the T4 DNA ligase was inactivated by maintaining the solution at 65° C. for 10 minutes. The end polynucleotides were kinased by mixing 52 µl of the above reaction, 4 µl of a solution containing 10 mM ATP and 5 units of T4 polynucleotide kinase. This solution was maintained at 37° C. for 30 minutes and then the T4 polynucleotide kinase was inactivated by maintaining the solution at 65° C. for 10 minutes.

TABLE 2

| 1. | 5' TGAATTCTAAACTAGTCGCCAAGGAGACAGTCAT 3'<br>(SEQUENCE ID NO. 13) |
|---|---|
| 2. | 5' AATGAAATACCTATTGCCTACGGCAGCCGCTGGATT 3'<br>(SEQUENCE ID NO. 14) |
| 3. | 5' GTTATTACTCGCTGCCCAACCAGCCATGGCC 3'<br>(SEQUENCE ID NO. 15) |
| 4. | 5' GAGCTCGTCAGTTCTAGAGTTAAGCGGCCG 3'<br>(SEQUENCE ID NO. 16) |
| 5. | 5' CTATTTCATTATGACTGTCTCCTTGGCGACTAGTTTAGAATTCAAGCT 3'<br>(SEQUENCE ID NO. 17) |

TABLE 2-continued 6. 5' CAGCGAGTAATAACAATCCAGCGGCTGCCGTAGGCAATAG 3'
   (SEQUENCE ID NO. 18)

7. 5' TGACGAGCTCGGCCATGGCTGGTTGGG 3'
   (SEQUENCE ID NO. 19)

8. 5' TCGACGGCCGCTTAACTCTAGAAC 3'
   (SEQUENCE ID NO. 20)

The completed synthetic DNA insert was ligated directly into the Lambda Zap™ II vector described in Example 1(a)(i) that had been previously digested with the restriction enzymes Sac I and Xho I. The ligation mixture was packaged according to the manufacture's instructions using Gigapack II Gold packing extract (Stratagene). The packaged ligation mixture was plated on XL1-Blue cells (Stratagene). Individual Lambda plaques were cored and the inserts excised according to the in vivo excision protocol for Lambda Zap™ II provided by the manufacturer (Stratagene). This in vivo excision protocol moved the cloned insert from the Lambda Lc2 vector into a plasmid phagemid vector allow for easy manipulation and sequendng. The accuracy of the above cloning steps was confirmed by sequencing the insert using the manufacture's instructions in the AMV Reverse Transcriptase $^{35}$S-dATP sequencing kit (Stratagene).

A preferred vector for use in this invention, designated Lambda Lc3, is a derivative of Lambda Lc2 prepared above. Lambda Lc2 contains a Spe I restriction site (ACTAGT) located 3' to the EcoR I restriction site and 5' to the Shine-Dalgarno ribosome binding site. A Spe I restriction site is also present in Lambda Hc2. A combinatorial vector, designated pComb, was constructed by combining portions of Lambda Hc2 and Lc2 together as described in Example 1a(iv) below. The resultant combinatorial pComb vector contained two Spe I restriction sites, one provided by Lambda Hc2 and one provided by Lambda Lc2, with an EcoR I site in between. Despite the presence of two Spe I restriction sites, DNA homologs having Spe I and EcoR I cohesive termini were successfully directionally ligated into a pComb expression vector previously digested with Spe I and EcoR I. The proximity of the EcoR I restriction site to the 3' Spe I site, provided by the Lc2 vector, inhibited the complete digestion of the 3' Spe I site. Thus, digesting pComb with Spe I and EcoR I did not result in removal of the EcoR I site between the two Spe I sites.

The presence of a second Spe I restriction site may be undesirable for ligations into a pComb vector digested only with Spe I as the region between the two sites would be eliminated. Therefore, a derivative of Lambda Lc2 lacking the second or 3' Spe I site, designated Lambda Lc3, is produced by first digesting Lambda Lc2 with Spe I to form a linearized vector. The ends are filled in to form blunt ends which are ligated together to result in Lambda Lc3 lacking a Spe I site. Lambda Lc3 is a preferred vector for use in constructing a combinatorial vector as described below.

(iv) Preparation of pComb

Phagemids were excised from the expression vectors lambda Hc2 or Lambda Lc2 using an in vivo excision protocol described above. Double stranded DNA was prepared from the phagemid-containing cells according to the methods described by Holmes, et al., (*Anal. Biochem.*, 114:193, 1981). The phagemids resulting from in vivo excision contained the same nucleotide sequences for anti- body fragment cloning and expression as did the parent vectors, and are designated phagemid Hc2 and Lc2, corresponding to Lambda Hc2 and Lc2, respectively.

For the construction of combinatorial phagemid vector pComb, produced by combining portions of phagemid Hc2 and phagemid Lc2, phagemid Hc2 was first digested with Sac I to remove the restriction site located 5' to the LacZ promoter. The linearized phagemid was then blunt ended with T4 polymerase and ligated to result in a Hc2 phagemid lacking a Sac I site. The modified Hc2 phagemid and the Lc2 phagemid were then separately restriction digested with Sca I and EcoR I to result in a Hc2 fragment having from 5' to 3' Sca I, not I Xho I, Spe I and EcoR I restriction sites and a Lc2 fragment having from 5' to 3' EcoR I, Sac I, Xba I and Sac I restriction sites. The linearized phagemids were then ligated together at their respective cohesive ends to form pComb, a circularized phagemid having a linear arrangement of restriction sites of Not I, Xho I, Spe I, EcoR I, Sac I, Xba I, Apa I and Sca I. The ligated phagemid vector was then inserted into an appropriate bacterial host and transformants were selected on the antibiotic ampicillin.

Selected ampicillin resistant transformants were screened for the presence of two Not I sites. The resulting ampicillin resistant combinatorial phagemid vector was designated pComb. The resultant combinatorial vector, pComb, consisted of a DNA molecule having two cassettes to express two fusion proteins and having nucleotide residue sequences for the following operatively linked elements listed in a 5' to 3' direction: a first cassette consisting of an inducible LacZ promoter upstream from the LacZ gene; a Not I restriction site; a ribosome binding site; a pelB leader; a spacer; a cloning region bordered by a 5' Xho and 3' Spe I restriction site; a decapeptide tag followed by expression control stop sequences; an EcoR I restriction site located 5' to a second cassette consisting of an expression control ribosome binding site; a pelB leader; a spacer region; a cloning region bordered by a 5' Sac I and a 3' Xba I restriction site followed by expression control stop sequences and a second Not I restriction site.

A preferred combinatorial vector designated pComb3, is constructed by combining portions of phagemid Hc2 and phagemid Lc3 as described above for preparing pComb. The resultant combinatorial vector, pComb3, consists of a DNA molecule having two cassettes identical to pComb to express two fusion proteins identically to pComb except that a second Spe I restriction site in the second cassette is eliminated.

b. Construction of Vector pCombIII for Expressing Fusion Proteins Having a Bacteriophage Coat Protein Membrane Anchor Because of the multiple endonuclease restriction cloning sites, the pComb phagemid expression vector prepared above is a useful cloning vehicle for modification for the preparation of an expression vector of this invention. To that end, pComb is digested with EcoR I and Spe I followed by phosphatase treatment to produce linearized pComb.

(ii) Preparation of pCombIII

A separate phagemid expression vector was constructed using sequences encoding bacteriophage cpIII membrane anchor domain. A PCR product defining the DNA sequence encoding the filamentous phage coat protein, cpIII, membrane anchor containing a LacZ promotor region sequence 3' to the membrane anchor for expression of the light chain and Spe I and EcoR I cohesive termini was prepared from M13mp 18, a commercially available bacteriophage vector (Pharmacia, Piscataway, N.J.).

To prepare a modified cpIII, replicative form DNA from M13mp18 was first isolated. Briefly, into 2 ml of LB (Luria-Bertani medium), 50 µl of a culture of a bacterial strain carrying an F' episome (JM107, JM109 or TG1) were admixed with a one tenth suspension of bacteriophage particles derived from a single plaque. The admixture was incubated for 4 to 5 hours at 37° C. with constant agitation. The admixture was then centrifuged at 12,000×g for 5 minutes to pellet the infected bacteria. After the supernatant was removed, the pellet was resuspended by vigorous vortexing in 100 µl of ice-cold solution I. Solution I was prepared by admixing 50 mM glucose, 10 mM EDTA (disodium ethylenediaminetetraacetic acid) and 25 mM Tris-HCl at pH 8.0, and autoclaving for 15 minutes.

To the bacterial suspension, 200 µl of freshly prepared Solution II was admixed and the tube was rapidly inverted five times. Solution II was prepared by admixing 0.2 N NaOH and 1% SDS. To the bacterial suspension, 150 µl of ice-cold Solution III was admixed and the tube was vortexed gently in an inverted position for 10 seconds to disperse Solution III through the viscous bacterial lysate. Solution III was prepared by admixing 60 ml of 5 M potassium acetate, 11.5 ml of glacial acetic acid and 28.5 ml of water The resultant bacterial lysate was then stored on ice for 5 minutes followed by centrifugation at 12,000×g for 5 minutes at 4° C. in a microfuge. The resultant supernatant was recovered and transferred to a new tube. To the supernatant was added an equal volume of phenol/chloroform and the admixture was vortexed. The admixture was then centrifuged at 12,000×g for 2 minutes in a microfuge. The resultant supernatant was transferred to a new tube and the double—stranded bacteriophage DNA was precipitated with 2 volumes of ethanol at room temperature. After allowing the admixture to stand at room temperature for 2 minutes, the admixture was centrifuged to pellet the DNA. The supernatant was removed and the pelleted replicative form DNA was resuspended in 25 µl of Tris-HCl at pH 7.6, and 10 mM EDTA (TE).

The double-stranded M13mp 18 replicative form DNA was then used as a template for isolating the gene encoding the membrane anchor domain at cpIII. M13mp 18 replicative form DNA was prepared as described above and used as a template for two PCR amplifications for construction of a DNA fragment consisting of the mature gene for cpIII membrane anchor domain located 5' to a sequence encoding the LacZ promoter, operator and cap-binding site for controlling light chain expression. The restriction sites, Spe I and EcoR I, were created in the amplification reactions and were located at the 5' and 3' ends of the fragment respectively. The procedure for creating this fragment by combining the products of two separate PCR amplifications is described below.

The primer pair, G-3(F) (SEQUENCE ID No. 21) and G-3(B) (SEQUENCE ID No. 22) listed in Table 3, was used in the first PCR reaction as performed above to amplify the cpIII membrane anchor gene and incorporate Spe I and Nhe I restriction sites into the fragment. For the PCR reaction, 2 µl containing 1 ng of M13mp 18 replicative form DNA were admixed with 10 µl of 10× PCR buffer purchased commercially (Promega Biotech, Madison, Wis.) in a 0.5 ml microfuge tube. To the DNA admixture, 8 µl of a 2.5 mM solution of dNTPs (dATP, dCTP, dGTP, dTTP) were admixed to result in a final concentration of 200 micromolar (µM). Three µl (equivalent to 60 picomoles (pM)) of the G-3(F) primer and 3 µl (60 pM) of the 3' backward G-3(B) primer were admixed into the DNA solution. To the admixture, 73 µl of sterile water and 1 µl/5 units of polymerase (Promega Biotech) were added. Two drops of mineral oil were placed on top of the admixture and 40 rounds of PCR amplification in a thermocycler were performed. The amplification cycle consisted of 52° C. for 2 minutes, 72° C. for 1.5 minutes and 91° C. for 2 minutes. The resultant PCR modified cpIII membrane anchor domain DNA fragment from M13mp 18 containing samples were then purified with Gene Clean (BIO101, La Jolla, Calif.), extracted twice with phenol/chloroform, once with chloroform followed by ethanol precipitation and were stored at −70° C. in 10 mM Tris-HCl at pH 7.5, and 1 mM EDTA.

The resultant PCR modified cpIII DNA fragment having Spe I and Nhe I sites in the 5' and 3' ends, respectively, of the fragment was verified by electrophoresis in a 1% agarose gel. The area in the agarose containing the modified cpIII DNA fragment was isolated from the agarose. The resultant amplified PCR fragment also contained nucleotide sequences for encoding a five amino acid tether composed of four glycine residues and one serine juxtaposed between the heavy chain and cpIII encoding domains. Once expressed, the five amino acid residue sequence lacking an orderly secondary structure served to minimize the interaction between the Fab and cpIII domains.

A second PCR amplification using the primer pairs, Lac-F (SEQUENCE ID No. 23) and Lac-B (SEQUENCE ID No. 24) listed in Table 3, was performed on a separate aliquot of M13mp 18 replicative form template DNA to amplify the LacZ promoter, operator and Cap-binding site having a 5' Nhe I site and a 3' EcoR I site. The primers used for this amplification were designed to incorporate a Nhe I site on the 5' end of the amplified fragment to overlap with a portion of the 3' end of the cpIII gene fragment and of the Nhe I site 3' to the amplified cpIII fragment. The reaction and purification of the PCR product was performed as described above.

An alternative Lac-B primer for use in constructing the cpIII membrane anchor and LacZ promotor region was Lac-B' as shown in Table 3. The amplification reactions were performed as described above with the exception that in the second PCR amplification, Lac-B' was used with Lac-F instead of Lac-B. The use of Lac-B' resulted in a LacZ region lacking 29 nucleotides on the 3' end but was functionally equivalent to the longer fragment produced with the Lac-F and Lac-B primers.

The products of the first and second PCR amplifications using the primer pairs G-3(F) and G-3(B) and Lac-F and Lac-B were then recombined at the nucleotides corresponding to cpIII membrane anchor overlap and Nhe I restriction site and subjected to a second round of PCR using the G-3(F) (SEQUENCE ID No. 21) and Lac-B (SEQUENCE ID No. 24) primer pair to form a recombined PCR DNA fragment product consisting of the following: a 5' Spe I restriction site; a cpIII DNA membrane anchor domain beginning at the nucleotide residue sequence which corresponds to the amino add residue 198 of the entire mature cpIII protein; an endogenous stop site provided by the membrane anchor at amino acid residue number 112; a Nhe I restriction site, a LacZ promoter, operator and Cap-binding site sequence; and a 3' EcoR I restriction site.

To construct a phagemid vector for the coordinate expression of a heavy chain-cpIII fusion protein with kappa light chain, the recombined PCR modified cpIII membrane anchor domain DNA fragment was then restriction digested with Spe I and EcoR I to produce a DNA fragment for directional ligation into a similarly digested pComb2 phagemid expression vector having only one Spe I site prepared in Example 1a4) to form a pComb2-III (also referred to as pComb2-III) phagemid expression vector. Thus, the resultant ampicillin resistance conferring pComb2-3 vector, having only one Spe I restriction site, contained separate LacZ promoter/operator sequences for directing the separate expression of the heavy chain (Fd)-cpIII fusion product and the light chain protein. The expressed proteins were directed to the periplasmic space by pelB leader sequences for functional assembly on the membrane. Inclusion of the phage F1 intergenic region in the vector allowed for packaging of single stranded phagemid with the aid of helper phage. The use of helper phage superinfection lead to expression of two forms of cpIII. Thus, normal phage morphogenesis was perturbed by competition between the Fab-cpIII fusion and the native cpIII of the helper phage for incorporation into the virion for Fab-cpVIII fusions. In addition, also contemplated for use in this invention are vectors conferring chloramphenicol resistance and the like.

A more preferred phagemid expression vector for use in this invention having additional restriction enzyme cloning sites, designated pComb-III' or pComb2-3', was prepared as described above for pComb2-3 with the addition of a 51 base pair fragment from pBluescript as described by Short, et al., *Nuc. Acids Res.*, 16:7583–7600 (1988) and commercially available from Stratagene. To prepare pComb2-3', pComb2-3 was first digested with Xho I and Spe I restriction enzymes to form a linearized pComb2-3. The vector pBluescript was digested with the same enzymes releasing a 51 base pair fragment containing the restriction enzyme sites Sal I, Acc I, Hinc II, Cla I, Hind II, EcoR V, Pst I, Sma I and BamH I. The 51 base pair fragment was ligated into the linearized pComb2-3 vector via the cohesive Xho I and Spe I termini to form pComb2-3'.

TABLE 3

| SEQ ID NO | | Primer | |
|---|---|---|---|
| (21)[1] | G-3 | (F) 5' | GAGACG<u>ACTAGT</u>GGTGGCGGTGGCTCTCCATTC<br><u>GTTTGTGAATATCAA</u> 3' |
| (22)[2] | G-3 | (B) 5' | TTACT<u>AGCTAGC</u>ATAATAACGGAATACCCAAAA<br><u>GAACTGG</u> 3' |
| (23)[3] | LAC-F | 5' | <u>TATGCTAGCTAGTAA</u>CACGACAGGTTTCCCGAC<br>TGG 3' |
| (24)[4] | LAC-B | 5' | ACCGAGCTC<u>GAATTC</u>GTAATCATGGTC 3' |
| (25)5 | LAC-B' | 5' | AGCTGTT<u>GAATTC</u>GTGAAATTGTTATCCGCT 3' |

F Forward Primer
B Backward Primer
1   From 5' to 3': Spe I restriction site sequence is single underlined; the overlapping sequence with the 5' end of cpIII is double underlined
2   From 5' to 3': Nhe I restriction site sequence is single underlined; the overlapping sequence with 3' end of cpIII is double underlined.
3   From 5' to 3': overlapping sequence with the 3' end of cpIII is double underlined; Nhe I restriction sequence begins with the nucleotide residue "G" at position 4 and extends 5 more residues = GCTAGC.
4   EcoR I restriction site sequence is single underlined.
5   Alternative backwards primer for amplifying LacZ; EcoR I restriction site sequence is single underlined.

EXAMPLE 2

ISOLATION OF HUMAN HSV-SPECIFIC MONOCLONAL ANTIBODIES PRODUCED FROM THE DICISTRONIC EXPRESSION VECTOR,PCOMB2-3

In practicing this invention, the heavy (Fd consisting of $V_H$ and $C_H1$) and light (kappa) chains ($V_L$, $C_L$) of antibodies are first targeted to the periplasm of *E. coli* for the assembly of heterodimeric Fab molecules. In order to obtain expression of antibody Fab libraries on a phage surface, the nucleotide residue sequences encoding either the Fd or light chains must be operatively linked to the nucleotide residue sequence encoding a filamentous bacteriophage coat protein membrane anchor. A coat protein for use in this invention in providing a membrane anchor is III (cpIII or cp3). In the Examples described herein, methods for operatively linking a nucleotide residue sequence encoding a Fd chain to a cpIII membrane anchor in a fusion protein of this invention are described.

In a phagemid vector, a first and second cistron consisting of translatable DNA sequences are operatively linked to form a dicistronic DNA molecule. Each cistron in the dicistronic DNA molecule is linked to DNA expression control sequences for the coordinate expression of a fusion protein, Fd-cpIII, and a kappa light chain.

The first cistron encodes a periplasmic secretion signal (pelB leader) operatively linked to the fusion protein, Fd-cpIII. The second cistron encodes a second pelB leader operatively linked to a kappa light chain. The presence of the pelB leader facilitates the coordinated but separate secretion of both the fusion protein and light chain from the bacterial cytoplasm into the periplasmic space.

In this process, the phagemid expression vector carries an ampicillin selectable resistance marker gene (beta lactamase or bla) in addition to the Fd-cpIII fusion and the kappa chain. The f1 phage origin of replication facilitates the generation of single stranded phagemid. The isopropyl thiogalactopyranoside (IPTG) induced expression of a dicistronic message encoding the Fd-cpIII fusion ($V_H$, $C_{H1}$, cpIII) and the light chain ($V_L$, $C_L$) leads to the formation of heavy and light chains. Each chain is delivered to the periplasmic space by the pelB leader sequence, which is subsequently cleaved. The heavy chain is anchored in the membrane by the cpIII membrane anchor domain while the light chain is secreted into the periplasm. The heavy chain in the presence of light chain assembles to form Fab molecules. This same result can be achieved if, in the alternative, the light chain is anchored in the membrane via a light chain fusion protein having a membrane anchor and heavy chain is secreted via a pelB leader into the periplasm.

With subsequent infection of *E. coli* with a helper phage, as the assembly of the filamentous bacteriophage progresses, the coat protein III is incorporated on the tail of the bacteriophage.

a. Preparation of Lymphocyte RNA

Five milliliters of bone marrow was removed by aspiration from a HIV-1 seropositive individual exhibiting a high titer (greater than 1:80) of antibodies to Herpes simplex virus (hereinafter referred to as HSV). Total cellular RNA was prepared from the bone marrow lymphocytes as described above using the RNA preparation methods described by Chomczynski, et al., *Anal Biochem.*, 162:156–159 (1987) and using the RNA isolation kit (Stratagene) according to the manufacturer's instructions. Briefly, for immediate homogenization of the cells in the isolated bone marrow, 10 ml of a denaturing solution containing 3.0 M guanidinium isothiocyanate containing 71 µl of beta-mercapto- were admixed to the isolated bone marrow. One ml of sodium acetate at a concentration of 2 M at pH 4.0 was then admixed with the homogenized cells. One ml of phenol that had been previously saturated with $H_2O$ was also admixed to the denaturing solution containing the homogenized spleen. Two ml of a chloroform:isoamyl alcohol (24:1 v/v) mixture was added to this homogenate. The homogenate were mixed vigorously for ten seconds and maintained on ice for 15 minutes. The homogenate was then transferred to a thick-walled 50 ml polypropylene centrifuged tube (Fisher Scientific Company, Pittsburgh, Pa.). The solution was centrifuged at 10,000×g for 20 minutes at 4° C. The upper RNA-containing aqueous layer was transferred to a fresh 50 ml polypropylene centrifuge tube and mixed with an equal volume of isopropyl alcohol. This solution was maintained at −20° C. for at least one hour to precipitate the RNA. The solution containing the precipitated RNA was centrifuged at 10,000×g for twenty minutes at 4° C. The pelleted total cellular RNA was collected and dissolved in 3 ml of the denaturing solution described above. Three ml of isopropyl alcohol were added to the re-suspended total cellular RNA and vigorously mixed. This solution was maintained at −20° C. for at least 1 hour to precipitate the RNA. The solution containing the precipitated RNA was centrifuged at 10,000×g for ten minutes at 4° C. The pelleted RNA was washed once with a solution containing 75% ethanol. The pelleted RNA was dried under vacuum for 15 minutes and then re-suspended in dimethyl pyrocarbonate-treated (DEPC-$H_2O$) $H_2O$.

Messenger RNA (mRNA) enriched for sequences containing long poly A tracts was prepared from the total cellular RNA using methods described in *Molecular Cloning: A Laboratory Manual*, Maniatis, et al., eds., Cold Spring Harbor, N.Y., (1982). Briefly, one half of the total RNA isolated from a single donor prepared as described above was resuspended in one ml of DEPC-$H_2O$ and maintained at 65° C for five minutes. One ml of 2× high saft loading buffer consisting of 100 mM Tris-HCl, 1 M NaCl, 2.0 mM EDTA at pH 7.5, and 0.2% SDS was admixed to the resuspended RNA and the mixture allowed to cool to room temperature.

The total purified mRNA was then used in PCR amplification reactions as described in Example 2b. Alternatively, the mRNA was further purified to poly A+ RNA by the following procedure. The total MRNA was applied to an oligo-dT (Collaborative Research Type 2 or Type 3) column that was previously prepared by washing the oligo-dT with a solution containing 0.1 M sodium hydroxide and 5 mM EDTA and then equilibrating the column with DEPC-$H_2O$. The eluate was collected in a sterile polypropylene tube and reapplied to the same column after heating the eluate for 5 minutes at 65° C. The oligo-dT column was then washed with 2 ml of high salt loading buffer consisting of 50 mM Tris-HCl at pH 7.5, 500 mM sodium chloride, 1 mM EDTA at pH 7.5 and 0.1% SDS. The oligo dT column was then washed with 2 ml of 1× medium salt buffer consisting of 50 mM Tris-HCl at pH 7.5, 100 mM, 1 mM EDTA and 0.1% SDS. The messenger RNA was eluted from the oligo-dT column with 1 ml of buffer consisting of 10 mM Tris-HCl at pH 7.5, 1 mM EDTA at pH 7.5, and 0.05% SDS. The messenger RNA was purified by extracting this solution with phenol/chloroform followed by a single extraction with 100% chloroform. The messenger RNA was concentrated by ethanol precipitation and resuspended in DEPC $H_2O$.

The resultant purified mRNA contained a plurality of anti-herpes simplex virus (HSV) antibodies encoding $V_H$ and $V_L$ sequences for preparation of an anti-HSV Fab DNA library.

EXAMPLE 3 a. Library construction, screening and Fab production

The preparation of human antibody Fab libraries displayed on the surface of M13 phage has been described above. The library was constructed as an IgG1×Fab library using bone marrow lymphocyte RNA of a long term asymptomatic HIV-1 positive individual. Antigen binding phage were selected against HSV-1 and -2 viral lysates (monkey kidney epithelial cells (VERO), 36 hr post infection, were pelleted and lysed using phosphate-buffered saline containing 1% sodium deoxycholate, 1% NP 40 (SIGMA), 0.1 mM DIFP and 2 mg/ml aprotinin) bound to EUSA wells (Sigma) through a panning procedure described in Burton, et al., *Proc. Nat'l. Acad. Sci. USA*, 88:10134–10137, 1991; Barbas, et al., *Methods*, 2:119–124, 1991. Phage from the final round of panning were converted to a soluble Fab expressing phagemid system and these clones selected for reactivity in ELISA with the antigen against which they were panned. Specific antibody was affinity purified from bacterial supernates over a protein A/G matrix (Shleicher & Schuell) as described in Williamson, et al., *Proc. Nat'l. Acad. Sci. USA*, 90:4141–4145, 1993.

b. Viruses and Cells

Vero cells were grown in RPMO 1640 supplemented with 5% fetal calf serum (FCS). HSV-1 and HSV-2 (strain F and G, respectively, ATCC, Rockville, Md.) were infected into Vero cells and virus titers were determined by plaque-assay and expressed as pfu ml$^{-1}$ c. Neutralization Activity

Crude E. coli extracts, positive in an ELISA screen using the same antigen preparation against which the library was panned, were tested for their ability to neutralize HSV-1 or HSV-2 at 1:5–1:10 dilutions according to the procedure described below. The Fabs that displayed neutralizing activity were affinity purified and their neutralizing titers were determined as follows. About 250 pfu of HSV-1 or HSV-2 were incubated with serial dilutions of recombinant Fabs for 1 hr at 37° C. and then adsorbed for 1 hr at 37° C. on Vero cell monolayers grown in six well plates. After adsorption, the inoculum was removed and the cells washed and overlaid with MEM containing 0.5% agarose and 2% FCS. After 72 hrs, the plates were fixed with 10% formaldehyde in phosphate-buffered saline (PBS) for 30 min, the nutrient agar overlay was removed and the cells were strained with a 1% solution of crystal violet in 70% methanol for 30 min. The stained monolayers were then washed and the plaques were counted.

d. Inhibition of Plaque Development Assay

Monolayers of Vero cells were infected with of 50–100 pfu of HSV-1 for 3 hrs at 37° C. They were then washed and the medium replaced with nutrient agar containing 25, 5 or 1 $\mu$g/ml of recombinant Fab. After 72 hrs or 86 hrs, they were fixed and stained as described above. Plaque diameter was measured with a digital caliper (Mitutoyo, Japan). At least 10 plaques were measured per well. Plaques below 0.2 mm in diameter were considered abortive and therefore not counted. Statistical calculations were performed by analysis of variants (Sheffe F-test).

e. Post-attachement Neutralization Assay

About 250 pfu of HSV-1 were adsorbed at 4° C. for 90 min on Vero monolayers prechilled at 4° C. for 15 min. The inoculum was then removed and the cells washed and overlaid with medium containing serial dilutions of recombinant Fab (5, 1, 0.2, 0.04 $\mu$g/ml) at 4° C. to prevent penetration of virus. After 90 min the Fab-contaning medium was removed and after washing, replaced with nutrient agar. For the purpose of control, equal amounts of virus were preincubated at 4° C. with serial dilutions (5, 1, 0.2, 0.04 $\mu$g/ml) of the same Fab (pre-attachment neutralization). After 90 min these virus/antibody dilutions were adsorbed onto Vero monolayers (prechilled at 4° C. for 1 hr and 45 min) for 90 min. The inoculum was then removed and the cells washed and overlaid with nutrient agar. After 72 hr, the monolayers were fixed and strained as described above for the neutralization assays.

f. Nucleic acid Sequencing

Nucleic acid sequencing was performed with a 373A automated DNA sequencer (Applied Biosystems) using a Taq fluorescent dideoxynucleotide terminator cycle sequencing kit (Applied Biosystems). Primers used for the elucidation of light and heavy chain sequence have been previously described in Williamson, et al., (*Proc. Nat'l Acad. Sci. USA*, 90:4141–4145, 1993).

g. Identification of antibody binding protein by immunoprecipitatlon

HSV-2 infected cells were harvested and sonicated in PBS containing 1% sodium deoxycholate, 1% NP40 (Sigma), 0.1 mM di-isopropylfluorophosphate (DIFP) and 2 mg/ml aprotinin. Lysates (50 $\mu$l) were then incubated with 7$\mu$g of recombinant Fab for 1 hour at 4° C. Immune complexes were precipitated with an agarose-bound goat anti-human (20 $\mu$l) resolved on a 10% SDS-PAGE and electro-blotted onto nylon membranes (BioRad) in 1× Towbin buffer. Western blots were performed according to standard protocols. Briefly, blots were blocked with 5% non-fat dry milk in Tris-buffered saline (TBS) and probed with a panel of established mouse monoclonal ant-HSV antibodies (Goodwin Institute) in 1% non-fat dry milk in TBS containing 0.05% Tween 20. Detection was performed with a goat anti-mouse antibody conjugated to alkaline phosphatase and chemiluminescence (BioRad). Blots were also immunoreacted with a rabbit polyclonal anti-HSV for the purpose of control and detected with a goat anti-rabbit antibody conjugated to alkaline phosphatase (BioRad).

h. Purification of Fabs

One liter cultures of super broth containing 50 $\mu$g/ml carbenicillin and 20 mM MgCl$_2$ were inoculated with appropriate clones and induced 7 hours later with 2 mM IPTG and grown overnight at 30° C. The cell pellets were sonicated and the supernatant concentrated to 50 ml. The fiftered supernatants were loaded on a 25 ml protein G-anti-Fab column, washed with 12 ml buffer at 3 ml/min., and eluted with citric acid, pH 2.3. The neutralized fractions were then concentrated and exchanged into 50 mM MES pH 6.0 and loaded onto a 2 ml Mono-S column at 1 ml/min. A gradient of 0–500 mM NaCl was run at 1 ml/min with the Fab eluting in the range of 200–250 mM NaCl. After concentration, the Fabs were positive when titered by ELISA against FG and gave a single band at 50 kD by 10–15% SDS-PAGE. Concentration was determined by absorbance measurement at 280 nm using an extinction coefficient (1 mg/ml) of 1.35.

EXAMPLE 4

NEUTRALIZING ACTIVITY OF Fab AGAINST HSV

A large panel of human combinatorial antibody Fab fragments specific for HSV-1 and -2 were isolated as described in Example 2. These antibodies were generated by independently panning an IgG1k Fab library of 2×10$^6$ members against whole lysate of these two viruses.

Enrichment of antigen specific phage, as determined by the number of phage eluted from HSV coated ELISA wells, was measured through 4 rounds of library panning. A 25-fold amplification was seen in the case of the panning with HSV-2 viral lysate, while a 20-fold amplification was observed using the HSV-1 viral lysate.

Soluble Fabs were then produced as described in Barbas, et al., *Proc. Nat'l Acad. Sci. USA* 88:7978–7982, 1991. Briefly, the phage coat protein III was excised from the phage display vector and the DNA self-ligated to give a vector producing soluble Fabs. Subsequently protein synthesis was induced overnight using IPTG and the bacterial pellet sonicated to release Fab from the periplasmic space. The Fab supernates were then tested, both in ELISA against the antigen with which they were panned and in immunofluorescence studies with virus-infected cells. Ten out of twenty clones taken from the final round of panning with HSV-1 viral lysate were positive in both assays, while 15 out of twenty were positive in the panning against HSV-2 lystate. All clones demonstrating positive reactivity with one virus type were further shown to be cross-reactive with the other in both immunofluorescence and ELISA assays. This probably reflects the known similarity between many of the proteins of HSV-1 and -2.

DNA sequences were determined as described above and the deduced amino acid sequences of the heavy chain variable domains were determined for several of the virus-specific clones (Table 4 and 5). Nine of 18 of the heavy chain sequences obtained from the HSV-2 panning were all quite different from each other. Similarly, 5 of 8 heavy chains taken from the HSV-1 panning were largely unrelated. A comparison of the targets to which these different antibodies are directed with the serum antibody reactivity of the donor indicates how accurately the library approach represents the humoral response of the donor to virus.

Although virus type cross-reactivity in ELISA was exhibited by all of the Fabs described here, only one heavy chain sequence was common to both pannings. Thus, despite the reported similarity between virions of HSV-1 and HSV-2 and the observed binding properties of the isolated Fabs, each virus selected distinct antibody molecules from the library. This implies differences between HSV-1 and -2 either in the antigens presented to the library or in the antibody response to the two viruses.

Neutralizing activity for all positive clones was estimated in plaque reduction and inhibition of plaque development assays of HSV-1 and -2, as described above. Three of the Fabs obtained from the HSV-2 panning exhibited a marked neutralization activity in both assays and with both virus types when tested as crude bacterial supernatants in vitro. These clones were shown to have identical heavy and light chain sequences. Accordingly, one of these Fab clones (Fab8), was grown in quantity, affinity purified and further characterized.

TABLE 4

|  | FR1 | CDR1 | FR2 | CDR2 |
|---|---|---|---|---|
| ACHSV1 15, 16, 20, 8 | LESGAEVKKPGSSVKVSCK5TSGGAFSFQG | SYAIN | WVRQAPGQGLEWHG | GILPVFGTTNHAQK-FQG |
| ACHSV1 15 | LEESGAEVKKPGSSVKVSCRASGGTFN | HYAIS | WVRQAPGQGLEWHG | GIFPFRNTAKYAQH-FQG |
| ACHSV1 13 | LEQSGAEVKKPGSSVKVSCKASGGSFS | SYAIN | WVRQAPGQGLEWHG | GLMPIFGTTNYAQK-FQD |
| ACHSV1 1 | LEESGGGLVKPGGSLRLSCTASGFIFS | DFYFS | WIRQPPGKGLEWLS | YIGGSHVYTNSADS-VKG |
| ACHSV1 2 | LESGGGLVQPGGSLRLSCAASGFTFS | GYAMN | WVRQAPGKGLEWVS | AISGNGFSTYYADS-VKG |

|  | FR3 | CDR3 | FR4 |
|---|---|---|---|
| ACHSV1 15, 16, 20, 8 | RVTFTADASTSTAYMELSSLRSEDTAVYYCAR | VGYCSTNGCSLGGMDV | WGQGTTVIVSS |
| ACHSV1 18 | RVTITADESTGTAYMELSSLRSEDTAIYYCAR | GDTIFGVTHGYYAMDV | WGQGTTVTVAS |
| ACHSV1 13 | RLTITADVSTSTAYMQLTGLTYEDTAMYYCAR | VAYMLEPTVTAGGLDV | WGQGTTVTVAS |
| ACHSV1 1 | RFTTSRDNAQKSLYLQMNSLRAEDTAVYYCAR | HSPETDGDTFDY | WGQGTLVIVPS |
| ACHSV1 2 | RFTISRDNARNTLYLQMNSLRAEDTAVYYCAK | VLLVATHYYYNGMDV | WGQGTTVTVSS |

Amino acid sequences of heavy chains generated by panning against HSV-1 lysate. Clone 13 heavy chain is identical to that of clones 1 and 8 derived from the panning against HSV-2.

TABLE 5

|  | FR1 | CDR1 | FR2 | CDR2 |
|---|---|---|---|---|
| ACHSV2 11 | LEESGAEMKKPGSSVRVSCKASGFTFH | NHAVS | WVRQAPGEGLEWMG | GLIPIVGLANLQPRFQG |
| ACHSV2 10, 15, 18, 20 | LEQSGAEVKKPGSSVKVSCKASGGTFS | SYAIH | WVRQAPGQGLEWMG | RITPMFSPAIYAQKFDG |
| ACHSV2 9 | LEESGAEVKKPGESLRITCKAVGYSFT | NAWIS | WVRQVPGKGLEWLG | RINPIDSSRNYSPSFQG |
| ACHSV2 8, 1 | LEQSGAEVKKPGSSVKVSCKASGGSFS | SYAIN | WVRQAPGQGLEWMG | GLMPIFGTTNYAQKFQD |
| ACHSV2 7, 16 | LESGPGLVKTSETLSLTCTVSGGSVSS | NSDYWA | WIRQTPGKGLEYFG | SILFGGTTYYNPSLKS |
| ACHSV2 2, 4, 5, 13 | LESGGGWQPGRSLRLSCAASGFTFR | TYGMH | WVRQAPGKGLEWVA | VISYDGSKNYYADSVKG |
| ACHSV2 14 | LEQSGGGWQPGRSLRLSCAASGFTFR | TYGMH | WVRQAPGKGLEWVA | VISYDGSKNYYADSVKG |
| ACHSV2 12 | LEQSGAELKRPWSSVKVSCKASGGTLR | STAVN | WVRQPPGQGLEWMG | GLIPLFGTPNYAQKFQG |
| ACHSV2 17 | LEQSGAEVKQPGSSMKVSCKVSGGIFR | TNAFS | WVRQAPGQGLEWMG | ISIPMFATVNYAGTFQG |
| ACHSV2 6 | LESGPGLVRPSETLFLTCSVSGASIN | SFFWS | WIRQSPGKGLEWIG | HIFHVGITNYNPSLKS |

|  | FR3 | CDR3 | FR4 |
|---|---|---|---|
| ACHSV2 11 | RVTISADESTNTAYMEMRSLTSDDTAIYYCVR | HGDDSSGFPPFDL | WGQGALVIVSS |
| ACHSV2 10, 15, 18, 20 | RVTITADESTTTAYMEMNSLRSDDTAVYYCAR | PSAYTGSLAY | WCQGTLVTVSS |
| ACHSV2 9 | HVTISADTSITSASLHWSSLEASDTAMYYCAR | HMSDSSGYSNRGAYDI | WGQGTMVIVPS |
| ACHSV2 8, 1 | RLTITADVSTSTAYMQLSGLTYEDTAMYYCAR | VAYMLEPTVTAGGLDV | WGQGTTVTVAS |

TABLE 5-continued

| | | | |
|---|---|---|---|
| ACHSV2 7, 16 | RVTMSVDTSTNQFSLDLSSVTMDTAVYYCAR | HTVTGFLEWSPPNWFFDL | WGRGTLVTVSS |
| ACHSV2 2, 4, 5, 13 | RFTISRDNSKKTLYLQMNSLRAEDTAVYYCAK | DFWSGSTKNVFDL | WGQGTLVTVSS |
| ACHSV2 14 | RFTISRDNSKKTLYLQMNSLRAEDTAVYYCAK | DFWSGSTKNVFDL | WGQGTLVTVSS |
| ACHSV2 12 | RVTFTADESTSTAYMELSSLRSDDTAVYYCAG | TSRGLNWFDP | WGQGALVTVSS |
| ACHSV2 17 | RITISADESTSWDMELSSLRPDDTAIYYCAR | GGRFLEFFEYGLDV | WGQGTTVIVSS |
| ACHSV2 6 | RVTMSVDKSKNQFSLRLNSVTMDTAVYYCVR | VKGLADGGTANWFDP | WGQGTLVTVSS |

Amino acid sequences of heavy chains selected by library panning against HSV2 lysate.

Figure 1B:
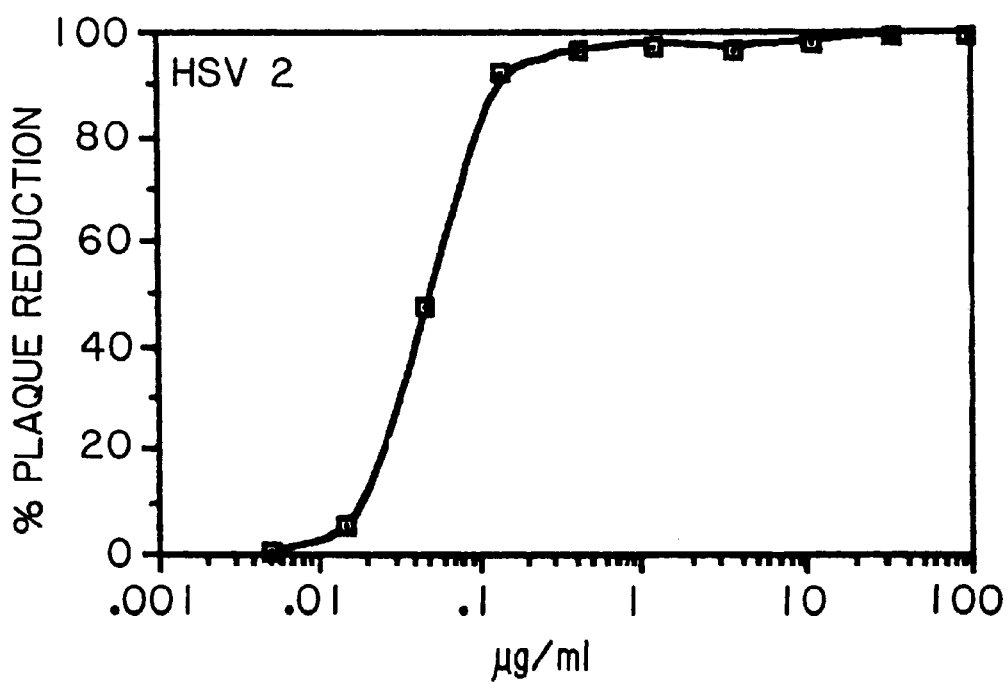
Figure 2A:
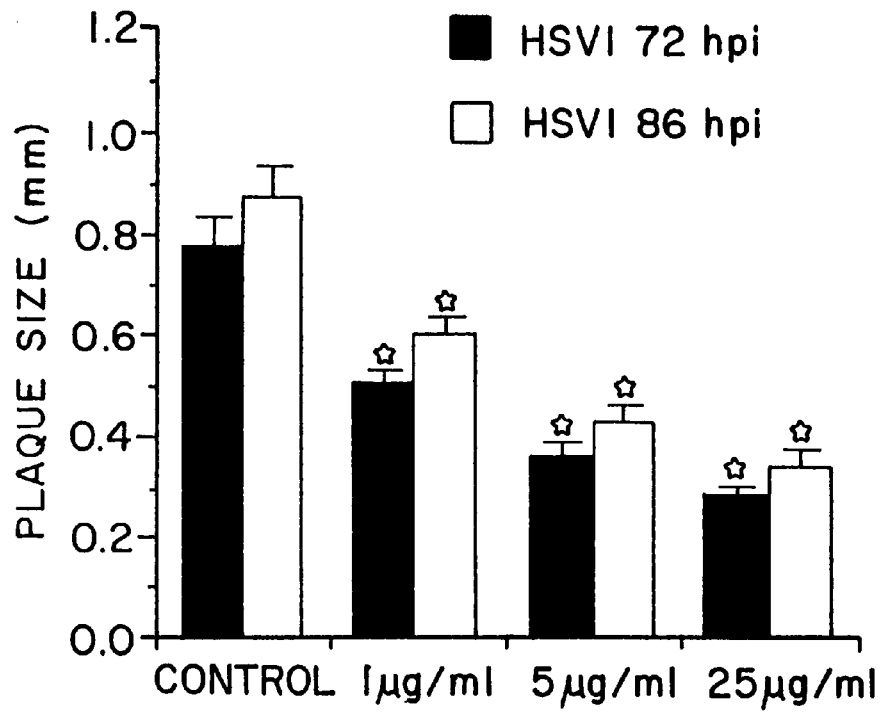
FIG. 2A shows statistically significant reduction in plaque size was observed at concentrations of 5 and 1 $\mu$g/ml (*=p<0.01), with an approximate 50% reduction in plaque size at 5 $\mu$g/ml. The number of plaques was also dramatically reduced at Fab concentrations of 5 and 25 $\mu$g/ml (FIG. 2B, FIG. 2D). At 25 $\mu$g/ml and 72 hrs hpi plaque development in HSV-2 infected monolayers was completely inhibited (FIG. 2C, FIG. 2D).
Figure 2B:
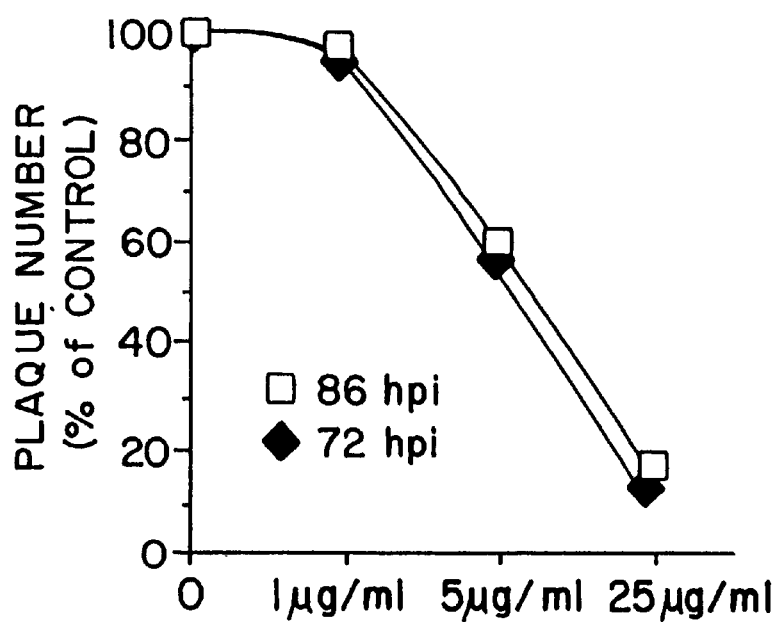
FIG. 2 shows an inhibition of plaque development assay. Purified Fab8 inhibited the development of plaques when applied 4 hours post-infection (hpi) on monolayers infected with HSV-1 (FIG. 2A, FIG. 2B) or HSV-2 (FIG. 2C, FIG. 2D) 4 hours post infection.
FIG. 2E shows an inhibition of plaque development assay with HSV-2 infected monolayers at a number of different Fab concentrations 86 hpi.
Figure 2C:
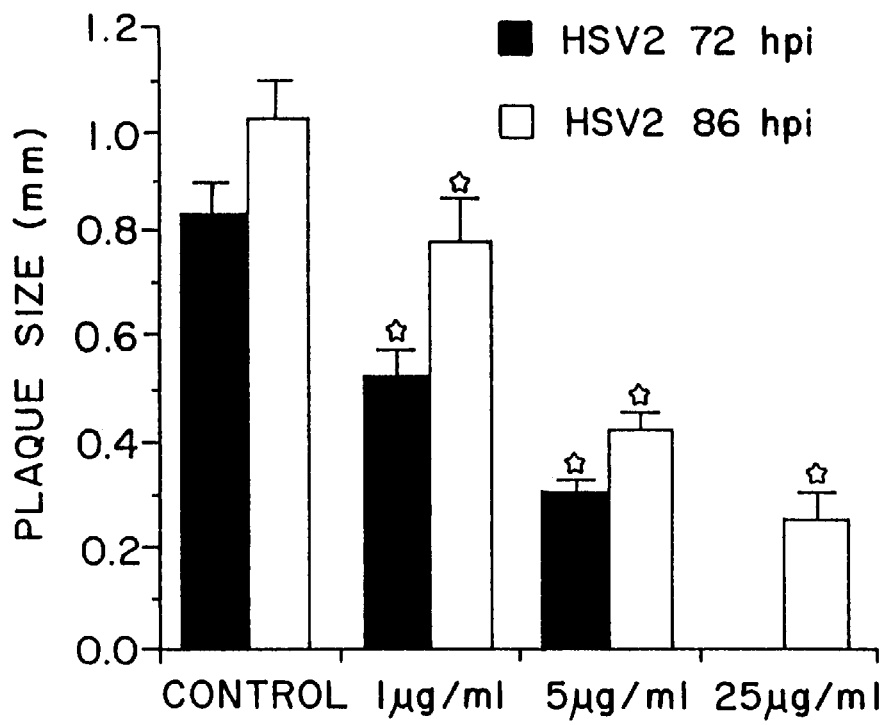
Figure 2D:
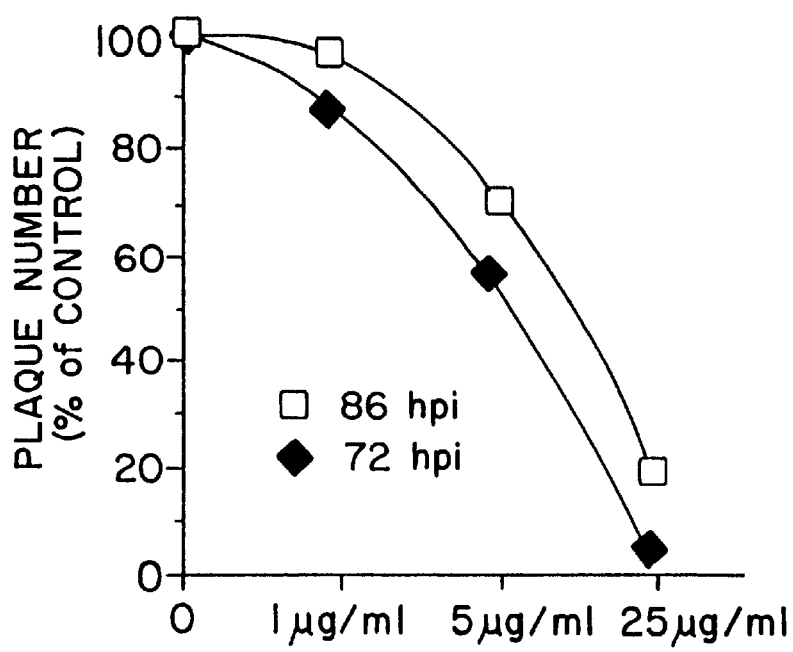
Figure 2E:
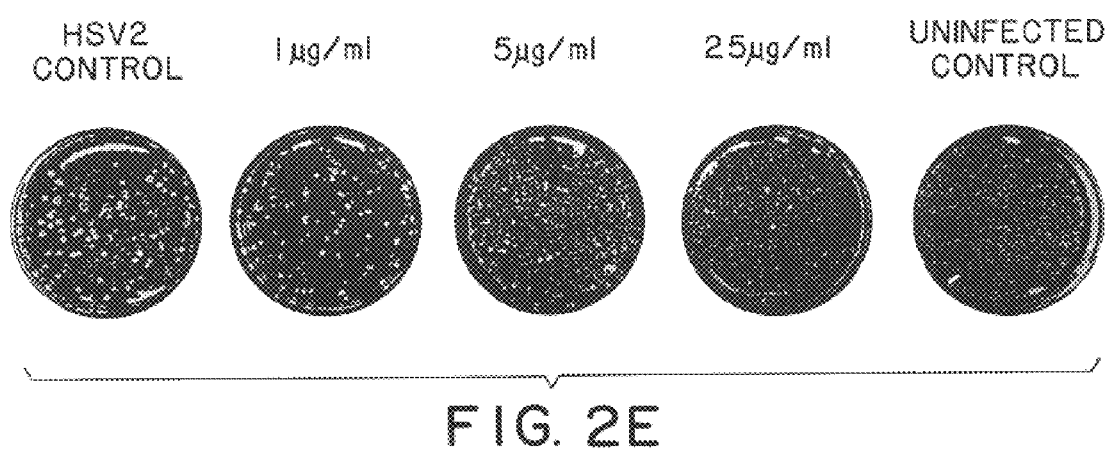

The Fab8 antibody was able to recognize both types of the virus. This antibody was shown to neutralize HSV-2 (50% inhibition at about 0.05 μg/ml) somewhat more efficiently than HSV-1 (50% inhibition at about 0.25 μg/ml and 80% inhibition at 0.6 μg/ml) (FIG. 1). FIG. 1 shows the neutralizing activity of Fab8, as measured by plaque reduction. FIG. 1A shows activity against HSV-1 and FIG. 1B shows activity against HSV-2. Purified Fab8 neutralized HSV-1 with a 50% inhibition at about 0.25 μg/ml and with an 80% inhibition at 0.6 μg/ml, while HSV-2 was neutralized with a 50% inhibition at about 0.05 μg/ml and an 80% inhibition at 0.1 μg/ml.

These figures suggest that Fab8 is approximately an order of magnitude more potent than most murine neutralizing antibodies described so far (Navarro, et al., *Virology*, 186:99–112, 1992; Fuller, et al., *J. Virol.*, 55:475–482, 1985), although recently reported anti-gB and anti-gD humanized murine antibodies may be equally potent (Deschamps, et al., *Proc. Nat'l Acad. Sci. USA*, 88:2869–2873, 1991). However, the mouse and humanized antibodies are bivalent whole IgG molecules rather than human derived Fab fragments. Also, eukaryotic expression of the recombinant Fab of the invention as an intact IgG molecule may significantly enhance its virus neutralization potency.

The Fab8 antibody also inhibited plaque formation when applied to virus-infected monolayers (FIG. 2). FIG. 2 shows an inhibition of plaque development assay. Purified Fab8 inhibited the development of plaques when applied 4 hours post-infection (hpi) on monolayers infected with HSV-1 (FIG. 2A, FIG. 2B) or HSV-2 (FIG. 2C, FIG. 2D) 4 hours post infection. FIG. 2A shows statistically significant reduction in plaque size was observed at concentrations of 5 and 1 μg/ml (*=p<0.01), with an approximate 50% reduction in plaque size at 5 μg/ml. The number of plaques was also dramatically reduced at Fab concentrations of 5 and 25 μg/ml (FIG. 2B, FIG. 2D). At 25 μg/ml and 72 hrs hpi plaque development in HSV-2 infected monolayers was completely inhibited (FIG. 2C, FIG. 2D). FIG. 2E shows an inhibition of plaque development assay with HSV-2 infected monolayers at a number of different Fab concentrations 86 hpi.

At a concentration of 25 μg/ml Fab8 completely abolished HSV-2 plaque development at 72 hrs post-infection, while a statistically significant reduction in plaque size (>50%) was observed at concentrations of 5 μg/ml and 1 μg/ml for both HSV-1 and HSV-2. Since it is accepted that plaques develop by spreading of virus to adjacent cells, the inhibition of plaque development assay determines the ability of an antibody to prevent cell-to-cell spread.

Figure 3A:
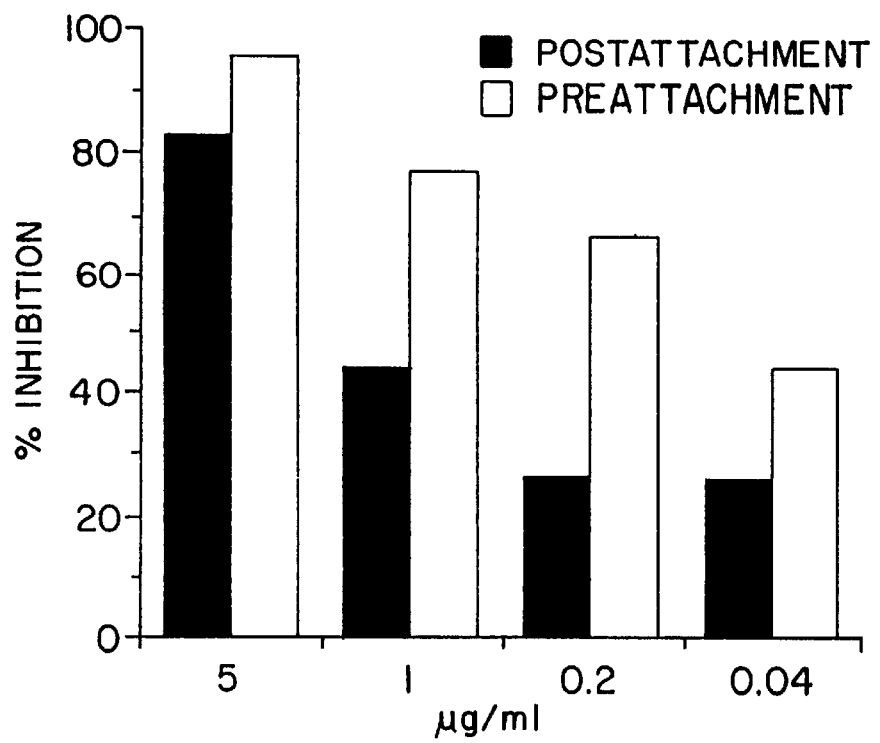
FIG. 3A shows the percentage of plaque reduction pre- and post-attachment at different Fab concentrations.
Figure 3B:
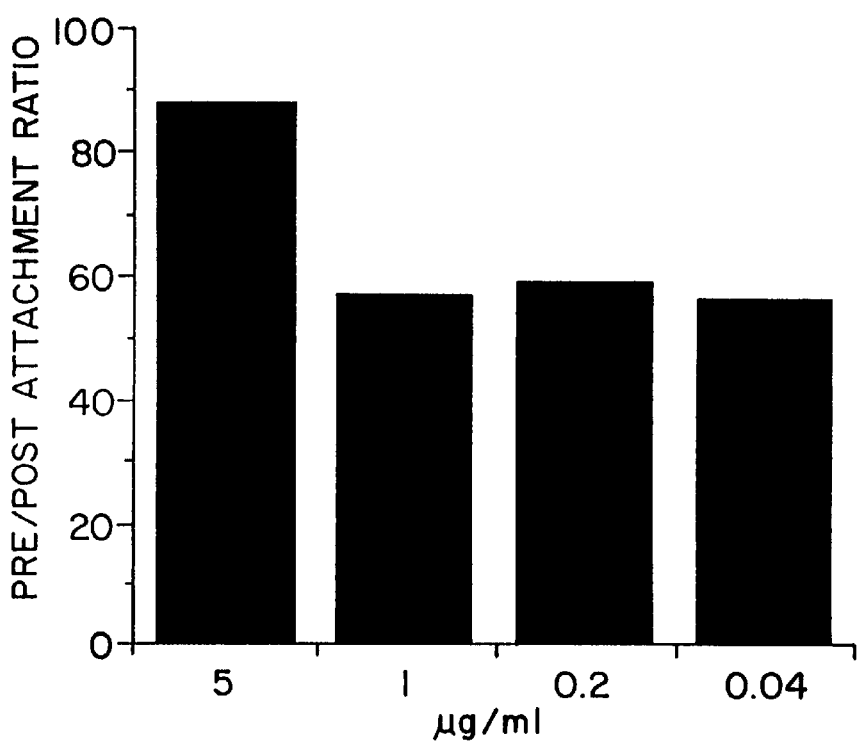
FIG. 3B shows the post-/pre-attachment neutralization ratio at different Fab concentrations.

Furthermore, this antibody strongly reduced infectivity after HSV-1 attachement (FIG. 3). FIG. 3 shows a post-attachment neutralization assay. Fab8 reduced HSV-1 infectivity after virion attachment. FIG. 3A shows the percentage of plaque reduction pre- and post-attachment at different Fab concentrations. FIG. 3B shows the post-/pre-attachment neutralization ratio at different Fab concentrations.

The pre-attachment/post attachment neutralization ratio was over 87% at an antibody concentration of 5 μg/ml, dropping to between 55–60% below 1 μg/ml. This suggests that the inhibitory action of the antibody takes place either at the level of membrane fusion, or during virus penetration or uncoating.

Figure 4:
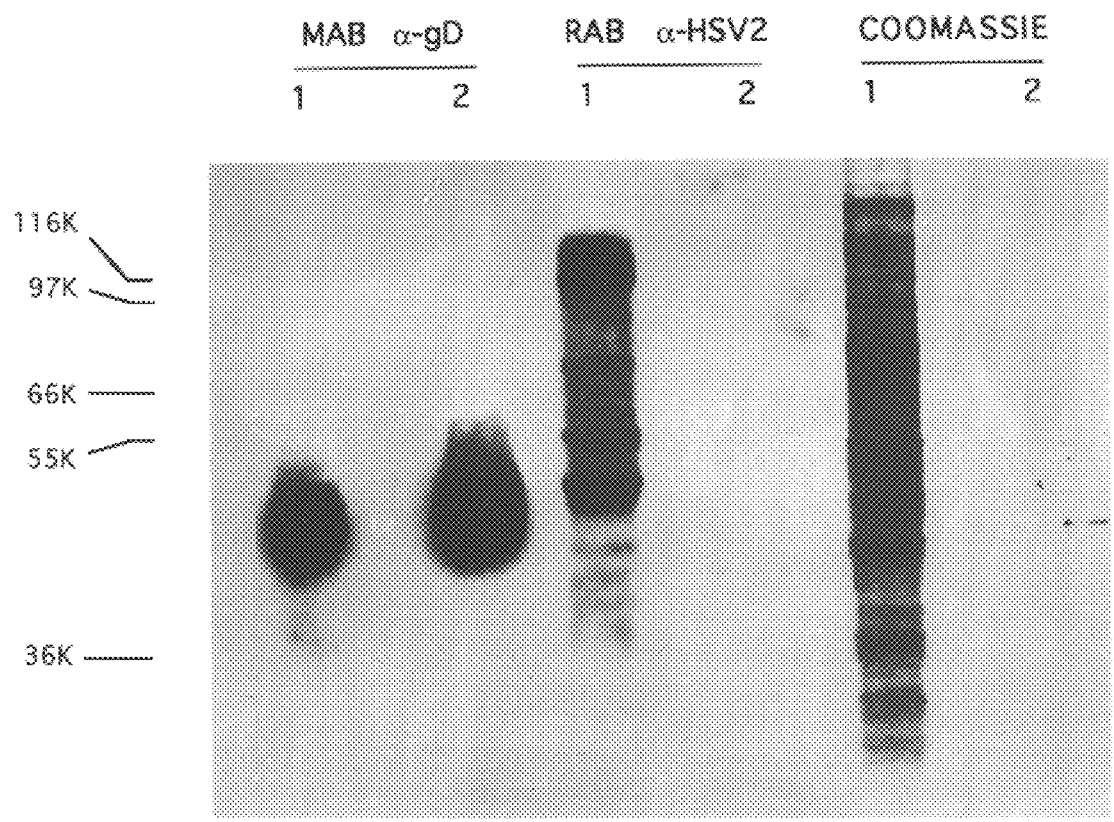
FIG. 4 shows the identification of the protein recognized by Fab8. SDS-PAGE of total proteins from HSV-2 infected Vero cells (lanes 1) and of the product of immunoprecipitation with Fab8 (lanes 2). Western blots performed in parallel were probed with a mouse monoclonal anti gD antibody (MAB $\alpha$-gD) and for the purpose of control, a rabbit polyclonal anti-HSV-2 preparation (RAB $\alpha$-HSV2). The Coomassie stain of a gel run in parallel is also shown. Fab8 immunoprecipitated a band of apparent molecular weight 48–50 kD which was recognized by a mouse monoclonal specific for gD, but not by mouse monoclonal antibodies against other HSV glycoproteins.

The protein recognized by Fab8 was identified via immunoprecipitation from whole lysate of HSV-2 infected cells. The precipitated proteins were blotted following resolution through SDS-PAGE and probed with a mouse monoclonal ant-gD and a rabbit polyclonal anti-HSV-2 (FIG. 4). FIG. 4 shows the identification of the protein recognized by Fab8. SDS-PAGE of total proteins from HSV-2 infected Vero cells (lanes 1) and of the product of immunoprecipitation with Fab8 (lanes 2). Western blots performed in parallel were probed with a mouse monoclonal anti gD antibody (MAB α-gD) and for the purpose of control, a rabbit polyclonal anti-HSV-2 preparation (RAB α-HSV2). The Coomassie stain of a gel run in parallel is also shown. Fab8 immunoprecipitated a band of apparent molecular weight 48–50 kD which was recognized by a mouse monoclonal specific for gD, but not by mouse monoclonal antibodies against other HSV glycoproteins.

The results illustrated in FIG. 4 show that the recombinant Fab recognizes a protein of mulecular weight approximately 48–50 kD that is also reactive with murine monoclonal anti-gD. No further proteins were detected on the blot by the rabbit ant-HSV-2 polyclonal antibody preparation thus confirming the specificity of the human Fab.

Fab8 has been shown to neutralize virus extremely efficiently and to inhibit viral spread from cell to cell. The demonstration of such antiviral activity by an Fab offers potential advantages over whole IgG for some in vivo applications. Although the serum haf life of Fab is dramatically shorter than that of whole IgG, the smaller molecule has far greater tissue penetration (Yokota, et al., *Cancer Research*, 52:3401–3408, 1992). The increased penetration of Fab also lends itself to potential topical applications. In the case of herpes this may take the form of an antibody cream to treat skin lesions, or as eyedrops for corneal Infections. Moreover, the use of a Fab may avoid inflammation arising from activation of effector mechanisms.

EXAMPLE 5

KINETICS OF NEUTRALIZATION OF HSV BY Fab8

Neutralization kinetics were performed according to standard techniques to examine the ability of Fab8 to neutralize HSV. Briefly, 10,000 plaque forming units (PFU)/ml of HSV type 11 strain G (ATCC VR739), Rockville, Md.) were incubated with three Fab8 different antibody concentrations (2, 6, 18 μg/ml). At different times 100 μl aliquots were removed and immediately diluted in 10 ml of prechilled PBS at 4° C. to terminate the antibody-antigen reaction. A standard plaque assay method was then used to determine the residual infectivity in these 1:100 dilutions. The residual infectivity expressed as number of plaques/initial viral inoculum (V/Vo) was plotted on a semilogaritmic plot.

Figure 5A:
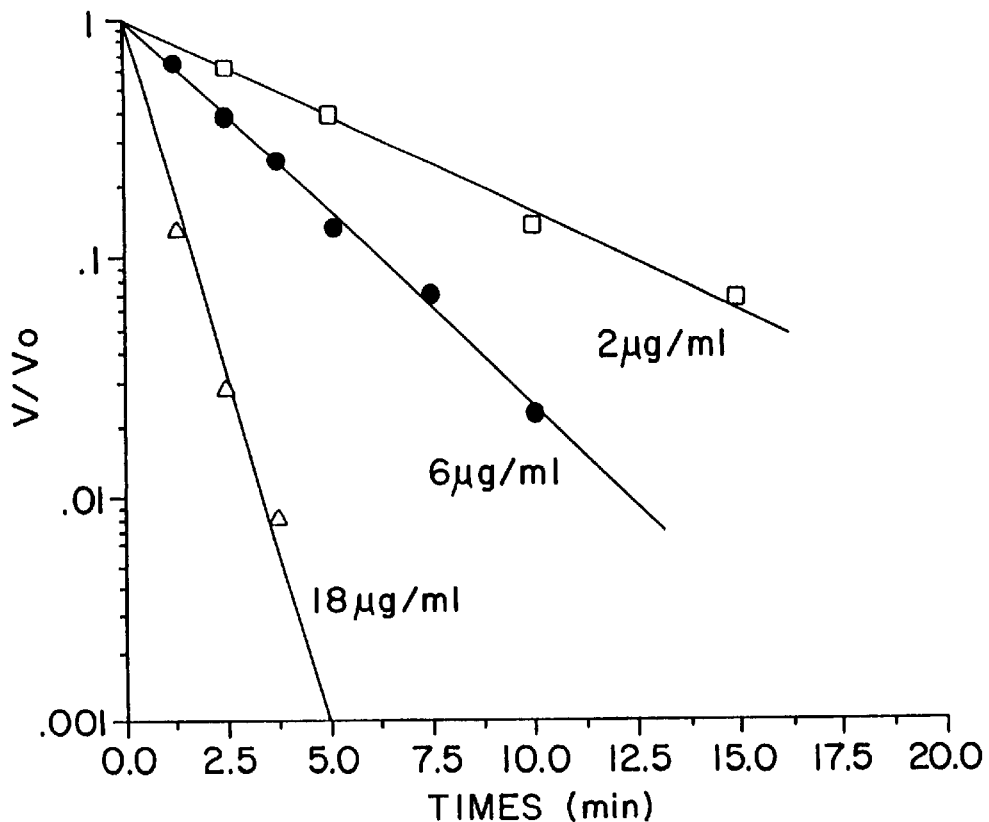
FIG. 5A shows the kinetics of neutralization of HSV Type-2, strain G (ATCC, Rockville, Md.) with Fab8. V/Vo is the number of viral plaque forming units present at time 0 (Vo) or after neutralization (V).
Figure 5B:
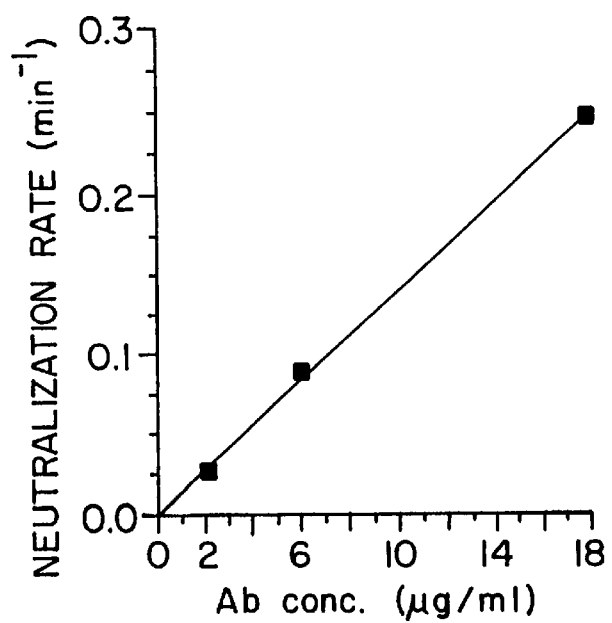
FIG. 5B shows the kinetics of neutralization of HSV Type-2, strain G (ATCC, Rockville, Md.) with Fab8. The neutralization rate is plotted versus the antibody concentration indicating first order kinetics.

FIG. 5A shows the kinetics of neutralization of HSV Type-2, strain G (ATCC, Rockville, Md.) with Fab8. V/Vo is the number of viral plaque forming units present at time 0 (Vo) or after neutralization (V). FIG. 5B shows the kinetics of neutralization of HSV Type-2, strain G (ATCC, Rockville, Md.) with Fab8. The neutralization rate is plotted versus the antibody concentration indicating first order kinetics.

Kinetic neutralization of HSV Type 2 strain G (ATCC, Rockville, Md.) display straight line profiles on semilog plot intercepting the ordinates at 1 (FIG. 5A). Furthermore, when the slopes of the lines obtained at different antibody concentrations are plotted versus the antibody concentrations they yield a straight line passing through the origin (FIG. 5B). The linearity of the two plots is suggestive of single hit (first order) kinetics, i.e., a single antibody molecule is sufficient to produce neutralization (Dulbecco, et al., *Virology*, 2:162, 1956).

TABLE 6

NEUTRALIZATION OF CLINICAL ISOLATES

The recombinant Fab was tested on six low passage clinical isolates of HSV type I and II which were all efficiently neutralized at similar antibody concentrations.

| Patient Initials | HSV Type | CLINICAL LOCALIZATION |
|---|---|---|
| F.Z. | II | foreskin |
| R.C. | II | vaginal |
| C.S. | II | vaginal |
| F.S. | I | lip (cold sore) |
| C.B. | I | lip (cold sore) |
| G.D. | I | gingivostomatitis |

The ability of this antibody to efficiently neutralize both laboratory strains and different clinical isolates of HSV type I and II suggests that the antibody interacts with a highly conserved and crucial neutralizing epitope and, therefore, may represent a potent therapeutical tool in clinical practice.

Figure 6:
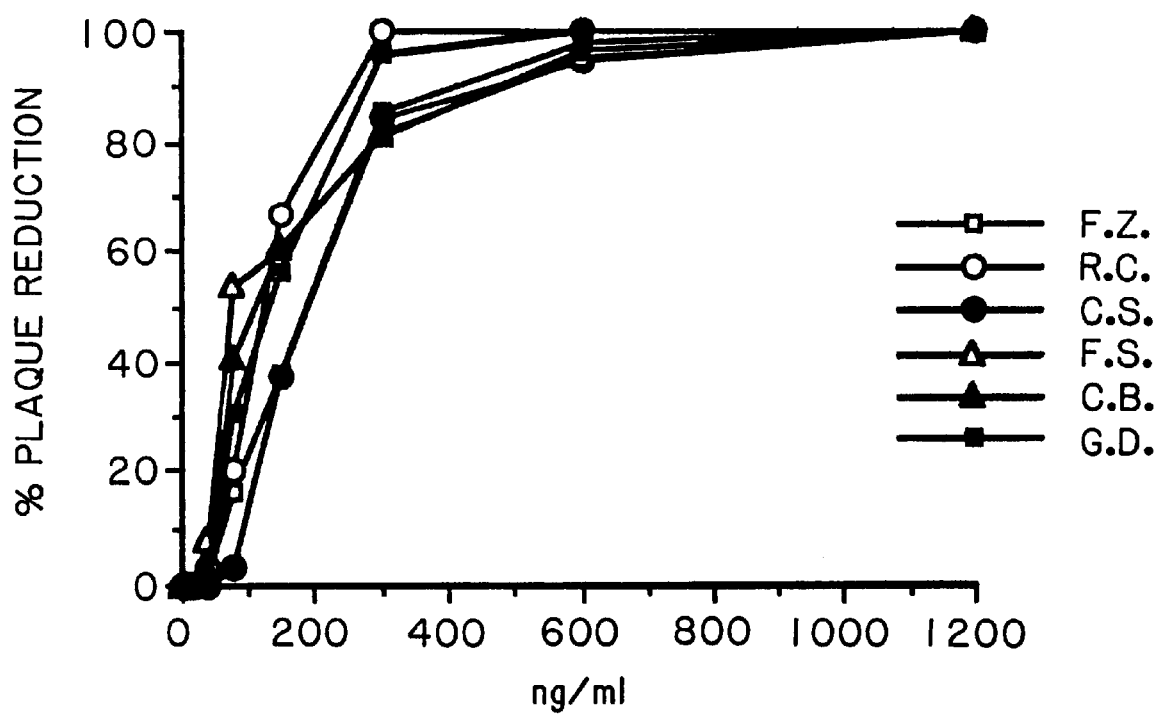
FIG. 6 shows the kinetics of neutralization of HSV Type-2, strain G (ATCC, Rockville, Md.) with Fab8. The plaque reduction is plotted versus antibody concentration for 6 different clinical isolates.

FIG. 6 shows a summary of the results shown in Table 6. The kinetics of neutralization of HSV Type-2, strain G (ATCC, Rockville, Md.) with Fab8 is shown. The plaque reduction is plotted versus antibody concentration for 6 different clinical isolates.

Deposit of Materials

The following plasmid has been deposited on Dec. 21, 1993, with the American Type Culture Collection, 1301 Parklawn Drive, Rockville, Md., 20852 USA (ATCC):

| Deposit | ATCC Accession No. |
|---|---|
| Clone FabHSV8 | ATCC 69522 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture for 30 years from the date of deposit. The bacteria will be made available by ATCC under the terms of the Budapest Treaty and applicants assure permanent and unrestricted availability of the progeny of the culture to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. §122 and the Commissioner's rules pursuant thereto (including 37 CFR §1.14 with particular reference to 886 OG 638). The assignee of the present application has agreed that if the culture deposit should die or be lost or destroyed when cultivated under suitable conditions, it will be promptly replaced on notification with a viable specimen of the same culture. Availability of the deposited strain is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the deposit, since the deposited embodiment is intended as a single illustration of one aspect of the invention and any plasmid that are functionally equivalent are within the scope of this invention. The deposit of material does not constitute an admission that the written description herein contained is inadequate to enable the practice of any aspect of the invention, including the best mode thereof, nor is it to be construed as limiting the scope of the claims to the specific illustration that it represents. Indeed, various modifications of the invention in addition to those shown and described herein will become apparent to those skilled in the art from the foregoing description and fall within the scope of the appended claims.

SEQUENCE ID LISTING

SEQUENCE ID NO 1 is the amino acid sequence for the CDR3 region of the heavy chain of clone FabHSV 8.

SEQUENCE ID NO 2 is the amino acid sequence for the heavy chain of FabHSV 8.

SEQUENCE ID NO 3–12 are nucleotide sequences for the polynucleotides for Lambda Hc2 construction.

SEQUENCE ID NO 13–20 are nucleotide sequences for the polynucleotides for Lambda Lc2 construction.

SEQUENCE ID NO 21–25 are nucleotide sequences for the primers for pCombIII construction.

We claim:

1. A human monoclonal antibody which neutralizes both Herpes simplex virus (HSV) Type 1 and Type 2, binds to an epitope present on glycoprotein D, has the binding specificity of an Fab fragment produced by ATCC 69522, and has heavy chains with a CDR of SEQ ID NO:1.

2. The human monolonal antibody of claim 1, which is an Fab fragment.

3. The human monoclonal antibody of claim 2, wherein the monoclonal antibody is an Fab fragment produced by ATCC 69500.

4. The human monoclonal antibody of claim 1, wherein the heavy chain comprises a CDR3 polypeptide sequence as in SEQUENCE ID No. 1.

5. The monoclonal antibody of claim 1 wherein the antibody is a single chain antibody.

6. A peptide which binds to an epitope present on glycoprotein D of both antigenic Type 1 and Type 2 of Herpes simplex virus (HSV) wherein the peptide has an amino acid sequence of SEQ ID NO:1.

7. A pharmaceutical composition comprising at least one dose of an immunotherapeutically effective amount of the monoclonal antibody of claim 1 in a pharmacological carrier.

8. A kit useful for the detection of Herpes simplex virus (HSV) in a source suspected of containing HSV, the kit comprising carrier means being compartmentalized to receive in close confinement therein one or more containers comprising a container containing the monoclonal antibody of claim 1.

* * * * *